(12) United States Patent
Mosher, Jr. et al.

(10) Patent No.: US 7,204,425 B2
(45) Date of Patent: Apr. 17, 2007

(54) ENHANCED IDENTIFICATION APPLIANCE

(75) Inventors: Walter W. Mosher, Jr., West Hills, CA (US); Michael L. Beigel, Encinitas, CA (US); H. Clark Bell, Chatsworth, CA (US); John Randall Tuttle, Boulder, CO (US); Oswaldo Penuela, Santa Clarita, CA (US); Samuel D. Y. Marcus, Encinitas, CA (US); David E. Wang, Newport Beach, CA (US)

(73) Assignee: Precision Dynamics Corporation, San Fernando, CA (US)

( * ) Notice: Subject to any disclaimer, the term of this patent is extended or adjusted under 35 U.S.C. 154(b) by 29 days.

(21) Appl. No.: 10/101,219

(22) Filed: Mar. 18, 2002

(65) Prior Publication Data

US 2003/0173408 A1    Sep. 18, 2003

(51) Int. Cl.
*G06K 19/06* (2006.01)
(52) U.S. Cl. .................... 235/492; 235/486; 235/375
(58) Field of Classification Search ........... 235/492, 235/479, 487, 486, 375; 342/357, 457, 419; 340/572.3, 572.5
See application file for complete search history.

(56) References Cited

U.S. PATENT DOCUMENTS

| | | | |
|---|---|---|---|
| 1,337,722 A | 4/1920 | Porter | |
| 3,197,899 A | 8/1965 | Twentier | |
| 4,154,011 A | 5/1979 | Rakestraw et al. | 40/21 C |
| 4,455,083 A * | 6/1984 | Elmes | 356/71 |
| 4,682,431 A | 7/1987 | Kowalchuk | 40/21 C |
| 4,835,372 A * | 5/1989 | Gombrich et al. | 235/375 |
| 4,882,861 A | 11/1989 | Holmes et al. | 40/299 |
| 4,991,337 A | 2/1991 | Solon | 40/633 |
| 4,993,068 A * | 2/1991 | Piosenka et al. | 713/186 |

(Continued)

FOREIGN PATENT DOCUMENTS

EP   0 777 171 B1   11/1996

(Continued)

OTHER PUBLICATIONS

Wolf Blitzer, *"Trusted Traveler' ID Cards?,"* CNN Wolf Blitzer Reports.

(Continued)

*Primary Examiner*—Kimberly D. Nguyen
(74) *Attorney, Agent, or Firm*—Kelly Lowry & Kelley LLC

(57) ABSTRACT

An enhanced identification appliance, such as a wristband, bracelet, patch, headband, neckband, ankleband, legband, card, sticker, or other wearable appliance, may have a biometric, chemical, optical, heat, pressure, humidity, electromagnetic, and/or acoustic sensor, various opto-electronics and/or various security features such as tamper-evident and tamper-resistant features. The sensors may obtain wearer-related information such as a fingerprint, retina, iris, blood, DNA, genetic data, voice pattern, temperature and other characteristic. Security features include a fastener on the identification appliance, which indicates whether the appliance has been attached to a wearer and if so, enables circuit functions. If one tampers with the appliance, circuit functions may be disabled, certain data erased, and/or evidence of tampering made apparent. The appliance may monitor the location or determine the identity of vehicle passengers for an airplane, train, boat, bus, etc. Alternatively, the identification band may contain a person's immigration status.

105 Claims, 15 Drawing Sheets

U.S. PATENT DOCUMENTS

| | | | |
|---|---|---|---|
| 5,026,084 A | 6/1991 | Pasfield | 283/75 |
| 5,145,211 A | 9/1992 | McKillip | 283/80 |
| 5,206,897 A * | 4/1993 | Goudreau et al. | 379/38 |
| 5,259,540 A | 11/1993 | Kocznar et al. | 224/219 |
| 5,311,689 A | 5/1994 | Lindsey | 40/633 |
| 5,395,667 A | 3/1995 | Ohno et al. | 428/40 |
| 5,423,574 A | 6/1995 | Forte-Pathroff | 283/75 |
| 5,448,846 A | 9/1995 | Peterson et al. | 40/633 |
| 5,457,906 A | 10/1995 | Mosher, Jr. | 40/633 |
| 5,479,797 A | 1/1996 | Peterson | 63/3 |
| 5,493,805 A | 2/1996 | Pennuela et al. | 40/633 |
| 5,581,924 A | 12/1996 | Peterson | 40/633 |
| 5,719,828 A | 2/1998 | Haas et al. | 368/327 |
| 5,742,233 A * | 4/1998 | Hoffman et al. | 340/573.1 |
| 5,748,148 A * | 5/1998 | Heiser et al. | 342/457 |
| 5,785,354 A | 7/1998 | Haas | 283/74 |
| 5,818,955 A | 10/1998 | Smithies et al. | 382/115 |
| 5,842,722 A | 12/1998 | Carlson | 283/107 |
| 5,844,244 A | 12/1998 | Graf et al. | 235/375 |
| 5,852,590 A * | 12/1998 | de la Huerga | 368/10 |
| 5,854,117 A | 12/1998 | Huisman et al. | 438/379 |
| 5,862,101 A | 1/1999 | Haas et al. | 368/327 |
| 5,877,675 A * | 3/1999 | Rebstock et al. | 340/286.07 |
| 5,883,576 A * | 3/1999 | De La Huerga | 340/573.1 |
| 5,889,489 A | 3/1999 | Friedman et al. | 342/51 |
| 5,903,246 A | 5/1999 | Dingwall | 345/82 |
| 5,905,461 A * | 5/1999 | Neher | 342/357.07 |
| 5,915,187 A | 6/1999 | Huisman et al. | 438/379 |
| 5,920,053 A * | 7/1999 | DeBrouse | 235/375 |
| 5,973,598 A | 10/1999 | Beigel | 340/572.1 |
| 5,973,600 A | 10/1999 | Mosher, Jr. | 340/572.8 |
| 5,978,493 A * | 11/1999 | Kravitz et al. | 382/115 |
| 5,995,048 A | 11/1999 | Smithgall et al. | 343/700 |
| 6,014,080 A * | 1/2000 | Layson, Jr. | 340/573.1 |
| 6,037,718 A | 3/2000 | Nagami | 315/169.3 |
| 6,045,652 A | 4/2000 | Tuttle et al. | 156/292 |
| 6,054,760 A | 4/2000 | Martinez-Tovar et al. | 257/692 |
| 6,064,751 A | 5/2000 | Smithies et al. | 382/115 |
| 6,068,192 A | 5/2000 | McCabe et al. | 235/487 |
| 6,069,969 A * | 5/2000 | Keagy et al. | 382/124 |
| 6,087,196 A | 7/2000 | Sturm et al. | 438/29 |
| RE36,843 E | 8/2000 | Lake et al. | 429/124 |
| 6,100,804 A | 8/2000 | Brady et al. | 340/572.7 |
| 6,111,549 A | 8/2000 | Feller | 343/795 |
| 6,118,379 A | 9/2000 | Kodukula et al. | 340/572.8 |
| 6,121,544 A | 9/2000 | Petsinger | 174/35 R |
| 6,122,494 A | 9/2000 | Tuttle | 455/193.1 |
| 6,127,977 A | 10/2000 | Cohen | 343/700 MS |
| 6,142,368 A | 11/2000 | Mullins et al. | 235/375 |
| 6,147,655 A | 11/2000 | Roesner | 343/741 |
| 6,177,859 B1 | 1/2001 | Tuttle et al. | 340/10.1 |
| 6,181,287 B1 | 1/2001 | Beigel | 343/741 |
| 6,189,783 B1 | 2/2001 | Motomiya et al. | 235/375 |
| 6,194,119 B1 | 2/2001 | Wolk et al. | 430/200 |
| 6,215,402 B1 | 4/2001 | Rao Kodukula et al. | 340/572.8 |
| 6,219,439 B1 | 4/2001 | Burger | 382/115 |
| 6,229,445 B1 | 5/2001 | Wack | 340/572.7 |
| 6,255,951 B1 * | 7/2001 | De La Huerga | 340/573.1 |
| 6,259,654 B1 * | 7/2001 | de la Huerga | 368/10 |
| 6,265,978 B1 | 7/2001 | Atlas | 340/575 |
| 6,346,886 B1 * | 2/2002 | De La Huerga | 340/573.1 |
| 6,388,612 B1 * | 5/2002 | Neher | 342/357.07 |
| 6,490,365 B2 * | 12/2002 | Horiguchi et al. | 382/117 |
| 6,577,751 B2 * | 6/2003 | Yamamoto | 382/117 |
| 2001/0020935 A1 | 9/2001 | Gelbman | 345/173 |
| 2001/0026240 A1 | 10/2001 | Neher | 342/357.07 |
| 2002/0084904 A1 * | 7/2002 | De La Huerga | 340/573.1 |

FOREIGN PATENT DOCUMENTS

| | | |
|---|---|---|
| EP | 0 851 377 A1 | 12/1997 |
| EP | 0 940 763 A1 | 12/1997 |
| EP | 1 033 687 A2 | 11/1999 |
| WO | WO 94/11190 | 5/1994 |
| WO | WO 96/04593 | 2/1996 |
| WO | WO 98/12670 | 3/1998 |
| WO | WO 98/23081 | 5/1998 |
| WO | WO 98/35393 | 8/1998 |
| WO | WO 99/09512 | 2/1999 |
| WO | WO 99/52422 | 10/1999 |
| WO | WO 99/56250 | 11/1999 |
| WO | WO 00/13588 | 3/2000 |
| WO | WO 00/16189 | 3/2000 |
| WO | WO 00/36566 | 6/2000 |
| WO | WO 01/17320 A1 | 3/2001 |
| WO | WO 01/20538 A2 | 3/2001 |
| WO | WO 01/26068 A1 | 4/2001 |
| WO | WO 01/26335 A2 | 4/2001 |
| WO | WO 01/27868 A1 | 4/2001 |
| WO | WO 01/37004 A1 | 5/2001 |
| WO | WO 01/39103 A1 | 5/2001 |
| WO | WO 01/41116 A1 | 6/2001 |
| WO | WO 01/46916 A2 | 6/2001 |
| WO | WO 01/54074 A1 | 7/2001 |
| WO | WO 01/61644 A1 | 8/2001 |

OTHER PUBLICATIONS

Ski Data Zermatt-Card.

* cited by examiner

ENHANCED IDENTIFICATION APPLIANCE

FIELD OF THE INVENTION

The field of the invention relates generally to identification appliances such as wristbands, and in particular to an identification appliance with a biometric sensor, chemical sensor, optical sensor, heat sensor, pressure sensor, humidity sensor, electromagnetic sensor, acoustic sensor, various opto-electronics and/or various security features such as tamper-evident and tamper-resistant features.

BACKGROUND OF THE INVENTION

This disclosure contemplates an improved identification wristband, bracelet, patch, headband, necklace, card, sticker, or other wearable appliance, which for the sake of convenience, are collectively referred to as a "band" or as a "identification appliance". Identification bands have become a convenient and effective way of identifying people without permanently marking them. A principle advantage of a band is that it is ultimately removable. Identification bands typically consist of a flexible wrist strap having a length greater than its width, and a closure or securement device for attaching and maintaining the band securely around the wearer's wrist. A portion of the band may be used for imprinting or otherwise attaching identification or other information regarding the wearer. Bar codes, radio frequency identification (RFID) devices and the like may also be used to store and transfer information associated with the band and the associated person or object. For example, RFID devices includes those which operate in the frequency in the range 30 kilohertz (kHz) to 300 Gigahertz (GHz). Various band constructions, attachments and other features including the storage of electronic data and RFID functions are described, for example, in Penuela U.S. Pat. No. 5,493,805, Mosher U.S. Pat. No. 5,457,906, Mosher U.S. Pat. No. 5,973,600, Beigel U.S. Pat. No. 5,973,598, Beigel U.S. Pat. No. 6,181,287, Peterson U.S. Pat. No. 5,479,797, and Peterson U.S. Pat. No. 5,581,924.

Bands are advantageous over other forms of ID cards containing data (such as credit cards, tickets or the like) since they can be attached to the wearer physically securely. As a result, current uses of identification bands include patient identification in hospitals, clinics and other locations; access in amusement parks; temporary security measures, facility access control, and ticketing and entitlement functions. While identification bands have been used for these purposes, additional applications for identification bands and the like are needed.

One important use for identification bands is patient identification and location in hospitals, clinics and other locations. When used in conjunction with an appropriate reader, patient information can be collected electronically and used by the medical staff in performance of their duties. Another example is to track the location of personnel such as convicts in a prison. When identification bands are used to designate who has authority to enter a restricted area, whether it be a concert hall or prison, the method of attachment of the identification band must be secure. Identification wristbands typically consist of a flexible wrist strap and a closure device for attaching and maintaining the wristband securely around the wearer's wrist. Further, an important aspect of identification bands, used for example in hospitals, jails, or hazardous work areas, is the security of the information contained in or on the band. In order to prevent fraud or mis-identification, it is desirable that the band and the associated information be securely and reliably maintained both physically and operationally. Although the prior art has attempted to make an identification band more secure, there is a need for further improvements.

Identification bands provide information simply, for example, by a person visually reading printed information on the band, scanning barcode information, or electronically reading identification information transmitted by the identification band. Thus, barcodes, RFID devices and the like are used to enhance the information storage and data transfer of information associated with the band and the associated person or object. There is a need to improve the type of information contained on an identification band as well as the manner in which the information is maintained.

Moreover, when an identification band incorporates wireless communications and data storage functions, opportunities for falsification and fraudulent use are increased. Of concern are insuring tamper detection, tamper prevention, secure transmission of information, the integrity of the information, and the prevention of unauthorized transfer of the information to others. Improvements in each of these areas are needed.

Information may be stored electronically in a transponder or RFID "tag" and that information is communicated to a tag "reader." Communication between the RFID tag and reader is by the transmission and reception of electromagnetic (EM) waves, and each must have an antenna to convert electrical signals to EM waves and vice versa. RFID systems can operate over a wide range of frequencies, including the high-frequency (HF) through super-high-frequency (SHF) radio bands, roughly 3 Megahertz (MHz) to 6 Gigahertz (GHz), such as 5.88 GHz, as well as frequencies in the vicinity of 400 MHz, 915 MHz, 2.45 GHz in the ultra-high frequency (UHF) band and 13.5 MHz. Coupling between the tag antenna and the reader antenna below about 50 MHz is primarily by the magnetic component of the reactive near field, in which the tag antenna is configured as a coil in a resonant circuit. Above 50 MHz, the transmission mechanism is the electric field in which the tag antenna is configured as a radiating element.

Because identification appliances may communicate with other devices, additional features and circuits may be desirable as well.

SUMMARY OF THE INVENTION

An identification appliance, such as a wristband, bracelet, patch, headband, neckband, ankleband, armband, belt, card, sticker, or other wearable appliance, is enhanced with a biometric sensor, chemical sensor, optical sensor, heat sensor, pressure sensor, humidity sensor, electromagnetic sensor, acoustic sensor, optical display, various opto-electronics and/or various security features such as tamper-evident and tamper-resistant features, as described herein. Also described are readers and verifiers for reading data from identification appliances, as well as applications for the identification appliance in passenger ticketing, passenger baggage checking and claiming, and immigration status.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE
PREFERRED EMBODIMENTS

As used in this specification, the meaning of "in," whether alone or in a compound such as "therein," includes "in" and "on"; "radio frequency identification" and "RFID" refer to identification by radio frequency communication.

Figure 1:
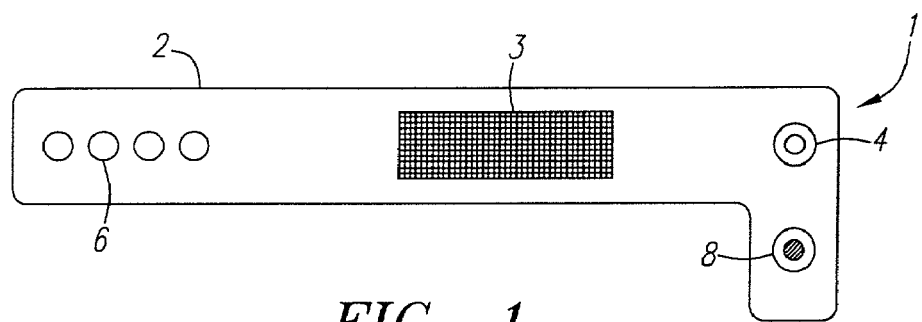
FIG. 1 illustrates an example of a prior art RFID wristband or bracelet.

FIG. 1 illustrates an example of a prior art RFID wristband or bracelet 1. The substrate 2 is an elongated flexible strip or laminate of polymer or paper. The RFID circuit 3 comprises antenna circuitry, signal generator circuitry, programmable encoder circuitry and interconnection circuitry. A fastener to adjustably and securely attach the wristband 1 comprises, on one end of the substrate 2, a snap fastener with parts 4 and 8, which can close over the other end of substrate 2, through one of the adjusting holes 6 therein, and snap together. Any of the embodiments described in this disclosure may include a fastener, which may be made adjustable, for example, by providing multiple mating or locking parts, a continuously variable length locking apparatus, or a unidirectional sizing locking apparatus (i.e., a known-type of fastener that allows a band to be made tighter, but not looser). The circuitry comprising the RFID circuit 3 can be, in various combinations, carried in the substrate 2, or formed by deposition on a layer in the substrate 2 of one or more of conductive paths, semiconductor devices, or polymer materials, in accordance with U.S. Pat. No. 5,973,598. The fastener can also comprise an adhesive wristband closure in accordance with U.S. Pat. No. 5,457,906, a closure mechanism in accordance with U.S. Pat. No. 5,479,797, a rivet, a staple, a crimp, or a heat-created bond, which securely attaches the ends of the wristband to each other and closes the wristband around the wearer's wrist.

Figure 2:
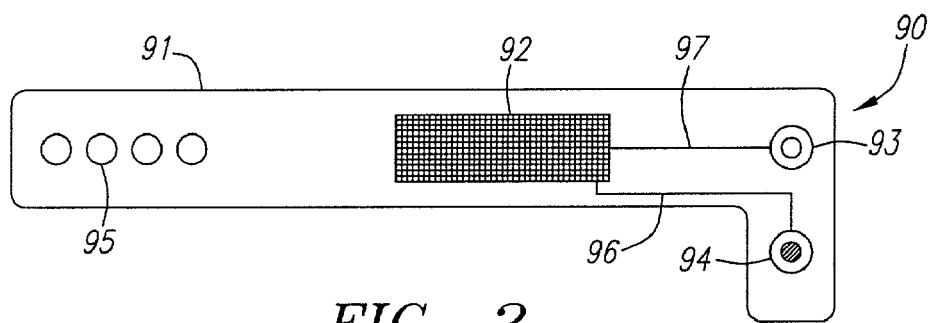
FIG. 2 is a representative illustration of an example embodiment of an improved secure identification band.

FIG. 2 illustrates an example embodiment of an improved secure identification band 90. As with any of the embodiments described in this disclosure, an identification "band" may comprise a wristband, bracelet, patch, headband, armband, legband, ankleband, fingerband, toe band, necklace, card, sticker, waistband, belt, or other wearable appliance. The identification band may include data that is perceivable to humans, animals, or machines. For example, the emission of an aerosol chemical or scent may be easily detectable by an animal such as a dog. Humans are intended fall under the "animal" category. Further, the data may be alphanumeric data, optical character recognizable data (such as bar codes), images, photographs, magnetically readable data, and/or biometric data. Biometric data refers to data, which can be used to identify a person such as the person's fingerprint, retina, blood, DNA, or voice data. In this particular example illustration, the identification band 90 includes a structure 91 that is suitable to be worn by, attached to, or carried by a person. Preferably, the identification band 90 is a wristband and the structure 91 is an elongate, flexible wristband material. For example, the structure 91 may be an elongated flexible strip or laminated combination of polymeric, paper, or organic substrate. As used in this specification, "organic" includes polymeric. However, the identification band 90 need not be attached only to the wrist of a person as it also can be attached to the ankle, neck, or other part of a person or animal, or to an object. The fastening of the band 90 closes a circuit 92 and enables circuit functions such as RFID functions. If desired, the opening of the fastener, opens or disables the circuit 92. The improved band 90 comprises a substrate structure 91, a circuit 92, a fastener with parts 93 and 94, adjusting holes 95, and conductors 96 and 97, which connect the circuit 92 to each fastener part 93 and 94. The fastener preferably closes an electronic circuit, makes an electrical connection when fastened, or otherwise enables an electronic circuit by, for example, electrical or capacitive coupling. Alternatively, the fastener may be electrically conductive. Still alternatively, the fastener may enable a circuit by inductive or magnetic coupling. As with any embodiment described in this disclosure, the circuit 92 preferably includes other circuits, such as antenna circuitry, communication circuitry, signal generator circuitry, programmable encoder circuitry and interconnection circuitry. Further and as with any embodiments in this disclosure, the circuit may perform a variety of functions including communication functions such as RFID. In one embodiment, a surface mount RFID chip containing electronic circuits is mounted within the identification band and electrically connected to an antenna. Alternatively, the RFID chip may be formed by deposition on a layer or layers in the structure 91, or on both sides of a layer in the structure 91. The circuitry comprising the communication circuit can be, in various combinations, carried in the substrate 91, or formed by deposition on a layer in the substrate 91 of one or more of conductive paths, semiconductor devices, or polymer materials. A circuit consisting entirely of conductive, insulating and/or semiconductive materials directly deposited on the substrate 91 may also be used. In fact, any of the circuits-on the identification band can be made either partially or totally from semiconductors, conductors and insulators, and may be fabricated of inorganic or organic materials, as described in U.S. Pat. No. 5,973,598, the entire disclosure of which is incorporated herein by reference for all purposes. An exemplary technique for forming an organic device, such as an organic semiconductor, is described in an article by Garnier et al. entitled "All-Polymer Field-Effect Transistor Realized by Printing Techniques" (Science, Vol. 265, Sep. 16, 1994), the entire article of which is incorporated herein by reference for all purposes. In other words, the identification band may have electronic components made either partially or totally from semiconductors, conductors and insulators, which may be inorganic or organic, and which may be printed on the identification band. U.S. Pat. No. 5,973,598 describes organic components, any of which may be used in the improved identification band. Further, a memory containing organic material is described in U.S. patent application Ser. No. 2001000817107, titled "Integrated Circuit Provided with a Substrate and with a Memory, Transponder, and Method of Programming a Memory," issued Nov. 29, 2001 to U.S. Philips Corp., the entirety of which is incorporated herein by reference for all purposes. It is preferable for the components of the identification band 90 to be thin so it is comfortable to wear. Additionally, it is preferable for the substrate 91 and the printed components to be flexible.

Further, as with any embodiment having a circuit, the circuit 92 of FIG. 2 may include a control logic or processing unit, which may be a microprocessor, microcontroller, central processing unit (CPU), arithmetic logic unit (ALU), math coprocessor, graphics processor, hardware controller, programmable logic device programmed for use as a controller, or other control logic. The circuit may include any of the circuits described in this disclosure or known to those of skill in the art of circuit design. As with any of the embodiments described in this disclosure, the circuit further may include an optional data storage device, such as a memory of any kind. The data storage device or memory may be fabricated out of inorganic materials, organic materials, or a combination of inorganic and organic materials. The identification band 90, and any of the identification bands described in this disclosure, may include an antenna such as a microstrip antenna described in co-pending U.S. patent application Ser. No. 10/093,202, titled "Microstrip Antenna for an Identification Appliance, filed on Mar. 5, 2002, and subsequently published on Sep. 11, 2003 as U.S. Publication 2003/0169207 whose entire disclosure is incorporated by reference for all purposes.

When the fastener closes, the parts 93 and 94 of the fastener come into contact, which closes the circuit 92 through the conductors 96 and 97, thereby enabling circuit functions. The conductors 96 and 97 may each comprise two or more separate electrical conductors that are connected to the circuit 92; the conductors further may comprise one or more of conductive wire or fiber, conductive foil, meltable conductor, or a printed conductor. In communication with the conductors is a fastener comprising one or more of a conductive adhesive, a conductive closure mechanism, a magnetic closure mechanism, a conductive rivet or staple, a crimped attachment, or a heat-created bond in proximity to the conductors, any of which when applied electrically connects, enables an electrical connection between, or alters the capacitance between, the conductors, thereby closing one or more electrical circuits, which may, for example, power the circuit 92, connect an antenna, tune the antenna, or change a logic state input to the circuit 92.

Other fasteners that can be used in any of the embodiments described in this disclosure include applying to the overlapping portions of the substrate one or more of the steps of permanently deforming the substrate to bond together the overlapped portions, rupturing walls of adhesive-filled microspaces in the substrate and optionally curing the adhesive by radio frequency, heat or ultraviolet exposure, rupturing walls of microspaces in the substrate separately filled with adhesive and catalyst that mix and cure thereupon, or by melting together adjacent surface areas of the overlapped portions, which when performed, securely attaches the ends of the wristband to each other, thereby closing the wristband around the wearer's wrist. As with any embodiment described in this disclosure, the fastener may enable a circuit by, for example, electrical, inductive, capacitative coupling.

Yet another alternative is to attach the identification band by a means similar to a belt buckle. For example, the buckle may be mounted to one end of the substrate 91 and which when opened, allows free movement of the other end of the substrate though the buckle so that the band be adjustably fitted to the wearer. The buckle design also permits removal of the identification band from the wearer for reuse. The buckle may comprise an electrical conductor and circuit-activating means to activate the circuit 92 when the identification band is fastened and to deactivate the circuit 92 when the identification band is unfastened or removed. The buckle can made of an electrically conductive metal of a type that is known to be suitable for buckles, including but not limited to an alloy of iron, copper or aluminum; the buckle can also be made of a polymer having an electrically conductive coating thereon. The circuit-activating means may comprise two separate electrical conductors in the substrate 91, each of which separately connects to the circuit 92 and extends toward the end of the substrate that does not have the buckle. When the buckle closes and clamps the substrate 91 between the movable and fixed portions of the buckle, a direct contact or a capacitive gap forms between each conductor and the buckle conductor, or the buckle alternatively brings together associated conductive surfaces, thereby closing an electrical circuit, which in turn activates the circuit 92. When the buckle is opened and the identification band is removed, the direct contact or capacitive gap between each conductor and the buckle conductor is broken, thereby opening the electrical circuit, which in turn deactivates the circuit 92.

The securement of the identification band may be permanent for the usage life of the band, or may be temporary and defeatable by an authorized procedure. In the case of temporary securement, the identification band may be re-used and re-secured using an authorized procedure or method by an authorized agency or person.

Any of the identification appliances or bands described in this disclosure may have electromagnetic energy absorption means so that the identification band may be energized by an external electromagnetic field signal. For example, an antenna may obtain power from a received signal, where the power is used to power some or all of the circuits on the identification appliance. The interrogating/powering electromagnetic signal provides power and enabling information to the identification band. The interrogating/powering signals may contain a power signal only or both a power signal and information modulated onto the power signal. Upon energizing by an electromagnetic signal, the identification band may display optically readable information according to the data programmed in the band, stored in the band, or received from the interrogating/enabling device.

Likewise, any of the identification appliance described in this disclosure may include an optional audio, visual, or sensory (e.g., vibrating) device to display information such as the scanned biometric data and alphanumeric information. The display may be a light emitting polymer diode, a liquid crystal display (LCD), or a diode-capacitor directly connected to an antenna that may be a resonant antenna. An example of a diode-capacitor is provided in U.S. patent application Ser. No. 09/723,897, titled "Rectifying Charge Storage Element" and filed on Nov. 28, 2000, the entirety of which application is incorporated herein by reference for all purposes. The diode-capacitor may, for example, include a LEDICAP, which is a diode-capacitor formed with a light-emitting polymer that emits light when current flows through it. The display can be always on, turned on by the circuit in the identification band, or activated by an external electromagnetic field signal. If an interrogating/powering electromagnetic signal includes a power signal and data modulated onto the power signal, the display may indicate only the presence of an interrogating or powering field, or it may indicate the data transmitted with the interrogating or powering field. Still alternatively, the display may indicate data derived from internal data in the identification band, a combination of information from both the identification band and the interrogating/powering field, or information derived from the band and/or the field.

The display may consist of a single device or a plurality of devices. A single device may be formed in an arbitrary shape, including an alphanumeric character, logo, or other recognizable symbol or picture. A plurality of devices may be formed into a matrix (row/column addressable) or another combination that creates a variety of different recognizable visual outputs such as pre-formed characters or symbols. The display may be based on an array of pixels. The display may be a flexible display formed on or attached to the substrate of the identification band. The display may be formed of reflective technologies such as electrophoretic, ferroelectric, cholesteric, or emissive technologies such as organic LED (OLED), PDLC (a reflective mode polymer-dispersed-liquid-crystal display) plasma, or cholesteric nematic (passive matrix LCD) technologies. A reflective display may be attached to or formed on the identification band, and the reflective display may be either volatile, where the display only produces an optical output when it is powered, or nonvolatile, where the display retains its optical state even after power is withdrawn from it. A nonvolatile display may be write-once or be reprogrammable. The display may provide information that is optically readable as image data by humans or machines, or a time-varying modulated optical signal (e.g., from a light-emitting diode or composite organic light-emitting device) that may be decoded remotely by an electro-optical receiver.

Any of the identification appliances or bands described in this disclosure may include an optional optical information transmission means so that information programmed or stored in the identification band may be transmitted optically as a modulated signal, through any of the known modulation techniques. Such an optical device may include silicon and organic or polymer light emitting diodes (LEDs).

Figure 3:
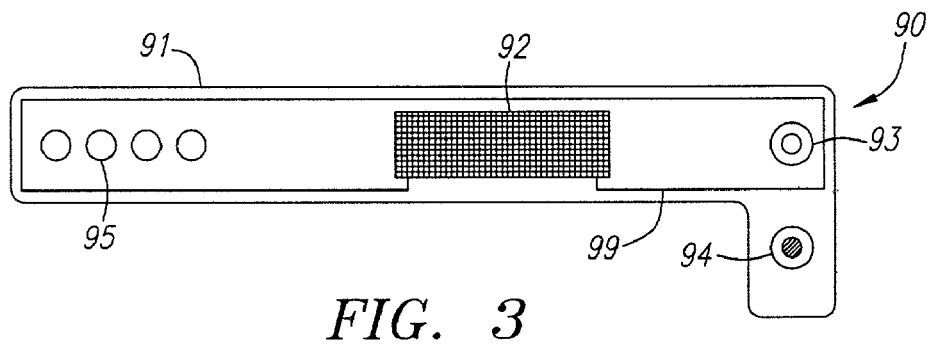
FIG. 3 is a representative illustration of another example embodiment of an improved secure identification band.

FIG. 3 illustrates another example embodiment of an improved secure identification band 90. The band 90 has a circuit 92 that opens and disables certain functions, such as communication or RFID functions, when the band is torn, cut, or overly stretched. The band 200 comprises at least one substrate 91, a circuit 92, a fastener with parts 93 and 94, adjusting holes 95, and a conductor 99 that forms a closed circuit with the circuit 92. When the band 90 is torn, cut, or overly stretched, the conductor 99 breaks, thereby opening the circuit and disabling circuit functions. The conductor 99 may comprise a pattern of electrical interconnections in the substrate 91, the conductors of which comprise one or more of a conductive wire or fiber, conductive foil, organic conductor, or printed conductor. When the band 90 is torn, cut, or overly stretched, the conductor 99 is severed or broken, thereby disconnecting portions of the circuit 92, which may in turn power the circuit 92 off, disconnect an antenna, detune the antenna, or change one or more logic state inputs to the circuit 92.

Alternatively, circuit functions can also be disabled by using a pattern of non-conductive fibers in the substrate 91 that are stronger than substrate and electrical interconnections therein; when the band 90 is stretched or twisted, the fibers tear the substrate 91 and rupture electrical circuits therein, which destroys or renders inoperative, for example, a data storage device in the circuit 92, a data transmission device in the circuit 92, some other circuit in the circuit 92, or the entire circuit 92. This alternative approach may be implemented in any of the other embodiments described in this disclosure.

Figure 4:
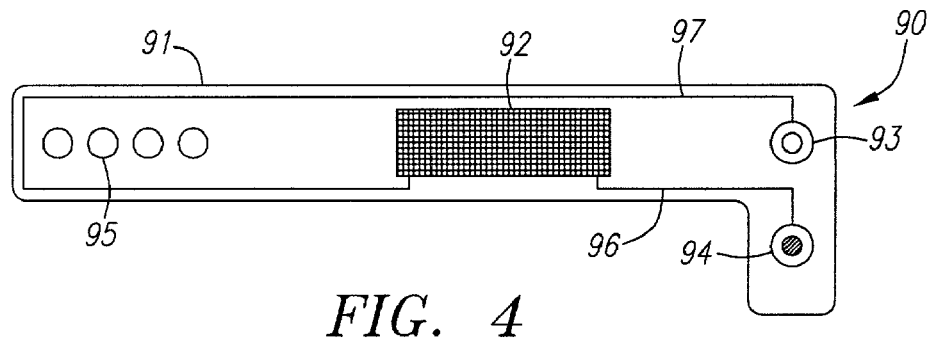
FIG. 4 is a representative illustration of yet another example embodiment of an improved secure identification band.

FIG. 4 illustrates yet another example embodiment of an improved secure identification band 90. Band 90 has a circuit 92 that closes and enables certain circuit functions when the band 90 is fastened and that opens and disables certain circuit functions when the band 90 is unfastened or is torn, cut, or overly stretched. As shown in FIG. 4, the band 90 comprises a substrate 91, a circuit 92, a fastener with parts 93 and 94, adjusting holes 95, and conductors 96 and 97 that connect the circuit 92 to each fastener part 93 and 94. The fastener preferably closes an electrical circuit or makes an electrical connection when fastened. Alternatively, the fastener may be electrically conductive. When the fastener closes, the parts 93 and 94 of the fastener come into contact, thereby closing the circuit 92 through the conductors 96 and 97 and enabling circuit functions. When the band 90 is unfastened, or is torn, cut, or overly stretched and conductor 96 or 97 breaks, the circuit opens and disables certain or all circuit functions. The conductors 96 and 97 may comprise two or more separate electrical conductors that are connected to the circuit 92, the conductors comprising one or more of conductive wire or fiber, conductive foil, meltable conductor, or a printed conductor. In communication with the conductors may be a fastener comprising one or more of a conductive adhesive, a conductive closure mechanism, a magnetic closure mechanism, a conductive rivet or staple, a crimp, or a heat-created bond in proximity to the conductors, any of which when applied electrically connects the conductors, enables an electrical connection between, or alters the capacitance between, the conductors, thereby closing one or more electrical circuits that may, for example, power the circuit 92, connect an antenna, tune the antenna, or change a logic state input to the circuit 92. When the electrical circuits are opened by unfastening, stretching, or cutting the band 90, portions of the circuit 92 are disconnected, which may power off portions or all of the circuit 92, disconnect an antenna, detune the antenna, or change a logic state input to the circuit 92. As previously mentioned, circuit functions can be disabled alternatively by using a pattern of non-conductive fibers in the substrate 91 that are stronger than substrate 91 and electrical interconnections therein. When the band 90 is overly stretched or twisted, the fibers tear or deform the substrate 91 and rupture electrical circuits therein, thereby destroying a data storage device in the circuit 92, a data transmission device in the circuit 92, any other circuit in the circuit 92, or the entire circuit 92.

Figure 5:
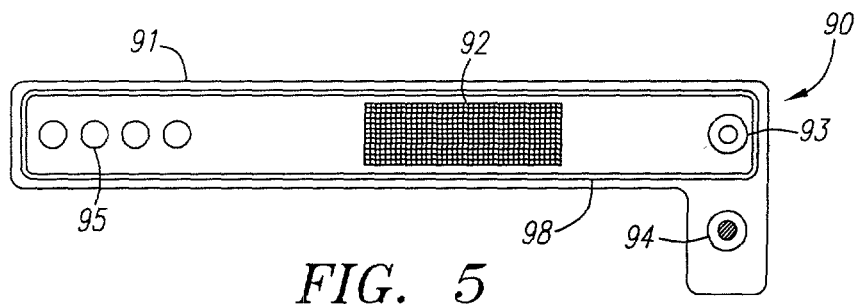
FIG. 5 is a representative illustration of yet another example embodiment of an improved secure identification band, which contains ink that is released by tampering.

FIG. 5 illustrates another example embodiment of an improved secure identification band containing an ink or dye that is released by tampering. As shown in FIG. 5, the example band 90 comprises a substrate 91, a circuit 92, a fastener with parts 93 and 94, adjusting holes 95, and container 98 containing an ink or dye that is released when the band 90 is torn, cut, or overly stretched. The ink-releasing means comprises an ink-filled space 98 in the band 90 and an empty space in the band 90 that is adjacent to the ink-filled space 98. When the band 90 is overly stretched, twisted, torn or cut, the wall ruptures between the ink-filled space 98 and the adjacent empty space, thereby leaking ink into the empty space and visibly discoloring the band 90. Alternatively, the wall ruptures between the ink-filled space 98 and the exterior surface of the band 90. In addition, the ink or dye may contain a chemical aerosol or scent perceivable by a machine (e.g., electronic chemical defecteor) or an animal, such as a dog or a human.

Alternatively, the identification band may be attached by means similar to a belt buckle, as previously discussed. For example, the buckle may be mounted to one end of the substrate 91 and which when opened, allows free movement of the other end of the substrate though the buckle so that the band be adjustably fitted to the wearer. The buckle design also permits removal of the identification band from the wearer for reuse. A dye tack in communication with the buckle releases dye when the buckle or dye-tack is subjected to tampering. The dye or ink tack may be similar to those used for retail theft deterrence, has locking parts that can be removed intact only with a special tool, and is attached in such a manner that a portion of the dye tack closes over or around a portion of the closed buckle. When an unauthorized attempt is made to open the buckle or to remove the dye tack from the identification band, a dye-filled vial in the dye tack is broken, thereby leaking dye out and discoloring identification band or marking the skin of the person who is tampering with the buckle or dye tack. Again, an aerosol chemical or scent may be contained in the dye tack, which is detectable to an animal, human, or machine.

Figure 6:
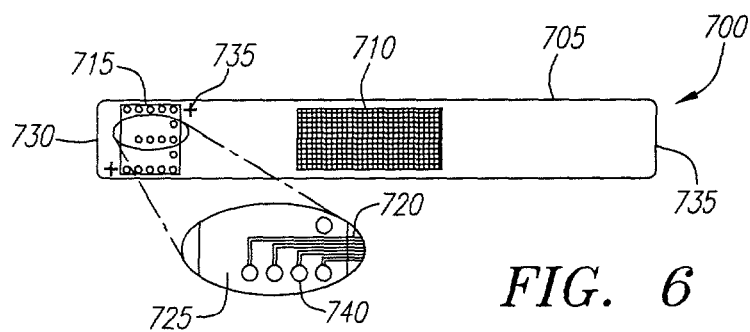
FIG. 6 is a representative illustration of still another example embodiment of an improved secure identification band, which, when attached, creates an identifying pattern in both visible and electronic forms.

FIG. 6 illustrates still another example embodiment of an improved identification band 700 that, when attached, creates an identifying pattern in both visible and electronic forms. As shown in FIG. 6, the example improved identification band 700 comprises a substrate 705 having a circuit 710 and an identification area 715 with a shaded background into which conductor pairs 720 from the circuit 710 terminate with connections 725. To attach the identification band 700, the first end 730 is placed over the second end 735, and holes 740 are punched through, or embossed into area 715 with the aid of alignment marks 735, thereby stitching together the overlapped ends, forming a visible pattern, and connecting and/or disconnecting specific pairs or random combinations of conductors 720 to form an electrical circuit of connected and/or disconnected pairs, which in turn set logic state inputs to the circuit 710 corresponding to the pattern. As with any of the embodiments, encoding the identity of a person, object or entity includes forming a unique pattern of one or more of an arrangement of figures, symbols or characters, a bar code, or a drawing corresponding to that identity. Forming a visible identification of the person, object or entity may include one or more of the following steps: forming an embossment, which embossment may include coloring with an ink; activating colorless material in the substrate to become colored; activating colorless adhesive and catalyst in the substrate to become colored when mixed or cured; and using a material or adhesive and catalyst that is sensitive to applied pressure or heat so as to make a visible pattern. Optionally, the embossed pattern may be visible only because of its contours. Applying the identifying pattern to the mechanical securement device includes one or more of mechanically, electrically, or thermally engraving, cutting, impressing, or embossing the pattern. In an example of the use of such a band 700, a number corresponding to a security clearance level of the wearer, such as the number "3", or an official seal can be applied at the time of attachment. Thus, a visible indication of that clearance, and an electronic indication based on the formed electrical circuit and transmitted by the circuit 710, are available for controlling access to a secure area or to classified information.

The data stored hi the identification band may include any kind of information. For instance, the data may comprise identity data, financial transaction data, or medical data. Any of the data may be encrypted prior to the data being stored in the identification band. As another example, bands with the same pattern and related information can be attached to a person and to a set of baggage, the pattern identifying both the person and an airline flight, so that only persons and baggage identified for that flight will be allowed on the aircraft, and the person can only claim baggage having bands with that same pattern.

An alternative to any of the embodiments described in this disclosure is to associate more than one identity with an identification band. For example, a first identifying pattern and a second identifying pattern may be stored or contained on the identification band. The first and second identifying patterns may manifest in different ways. As an example, the first identifying pattern forms a visible first identification, while the second identifying pattern forms electrical data in a data storage device in the identification band. Moreover, the first and second identifying patterns may be used to identify the same or different people. For instance, the first identifying pattern may be associated with the person who is distributing or attaching the identification band and the second identifying pattern may be associated with the wearer of the identification band.

A battery or power source may be provided to power a memory, logic, circuit, or other function of the identification band essential to its useful operation. In order to safeguard the security of information stored in the identification band in any of the embodiments described, the identification band may have a battery that runs out of power at or within a predetermined time period or on a certain calendar date/time, or a circuit that stops its operation or erases the stored information at or within a predetermined time period or on a certain calendar date/time. To make the battery life run out, the circuit may impose a fixed load on the battery, a programmable constant load on the battery, or upon the expiration of a timer, impose a load on the battery. Alternatively, the identification band may have a lock mode for data-stored in a data storage device such as a memory such that the data is not accessible without the proper equipment, password, and/or matching of identifying data with the user trying to gain access to the information.

Figure 7:
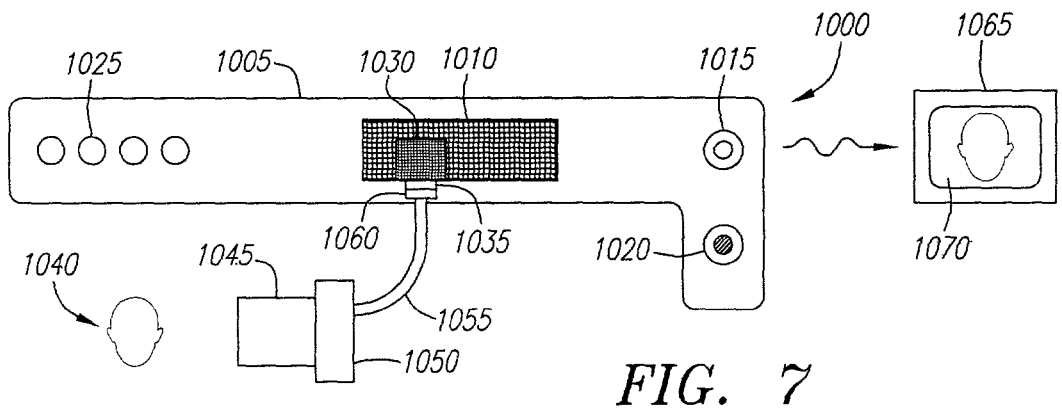
FIG. 7 is a representative illustration of an example embodiment of an improved identification band that stores biometric information.

FIG. 7 illustrates an example embodiment of an improved identification band that stores biometric information. As shown in FIG. 7, the improved band 1000 comprises a substrate 1005 having a circuit 1010, a fastener with parts 1015 and 1020, adjusting holes 1025, a data storage device 1030 that is preferably a nonvolatile memory, and a jack or electrical contacts 1035 for receiving biometric information to be stored in the data storage device 1030. For example and as with any embodiment described in this disclosure that may have a data storage device, the data storage device 1030 may be a random access memory (RAM), read only memory (ROM), programmable read only memory (PROM), electrically erasable PROM (EEPROM), organic PROM, organic RAM, anti-fuse PROM, ultraviolet light erasable PROM (UVPROM), fixed disk media, flexible disk media, flash memory, tape, or any other storage retrieval means, or any combination of these volatile and non-volatile memory means. The data storage device or memory can include any of the data storage devices or memories described in this disclosure or known to those of skill in the art of such devices. Also, as with any embodiment described in this disclosure, the data storage device or memory may further permit reading only, reading and writing, or writing only.

Further, as with any embodiment, the data storage device may store a link or address to information stored in an external database. This external database, which may be resident on an external system such as a computer, host system, or wireless network, and can preferably be accessed through the Internet. In such a case, the identification appliance transmits the link or address to the information in the database, whereupon receipt, the receiving device accesses the database and retrieves the actual information. This allows the data storage device to store less information locally, which can make the identification appliance smaller and thinner, while not sacrificing the amount of information being transferred. As an example, the database may store the entire medical history of the authorized bearer of the identification appliance, which medical history may be stored on the hospital's computer and which the hospital may update. Thus, by providing a pointer or link to the medical history, the information will be the most recent version and other people may add to, delete from, or otherwise modify the information, if desired. In another example, the database may store the digitized fingerprint data of the authorized bearer of the identification appliance, which can require a large amount of storage space that cannot be readily put onto the identification appliance.

As an example of the use of the improved band shown in FIG. 7, at the time of attachment of the band 1000 to a wearer 1040, the wearer 1040 is scanned by a charge-coupled device camera 1045 communicating with an encoder 1050 that converts the image signal to encoded image data and transmits that data through a cable 1055, a removable plug 1060 inserted into jack 1035, and into the data-storage device 1030. After attachment of the band 1000 and storage of the image data therein, the plug 1060 is detached from the jack 1035 and the wearer 1040 is free to move around. To later ascertain or verify the identity of the wearer 1040, the image data is transmitted by the circuit 1010 to a reader 1065, such as a RFID reader, decoded and rendered into a viewable image 1070, and then compared with the actual appearance of the wearer 1040.

Optionally, biological characteristics of the wearer 1040 may be stored in the band 1000 by transferring encoded biometric data to the data storage device 1030 on the band 1000 by electric current, electric or magnetic fields, or electromagnetic waves. For example, biometric data may include any images of or data about the wearer's fingerprints, retina, iris, face, DNA, genetic data such as a portion of the wearer's genome sequence or genes, or a time domain or frequency domain response of the wearer's voice, or a biochemical assay of the wearer's scent, blood, or breath. In other applications, the biometric data may be related to a person's signature, signature plus handwriting dynamics, iris, retina, face recognition, voiceprint, voiceprint and voice stress, fingerprint, other skin pattern, chemical signature (e.g., smell, blood, sweat), DNA, genetic data, or some electric, magnetic, acoustic, or other biometric characteristic. Alternatively, the biometric sensor may provide data about the wearer for purposes other than for identification. For instance, the biometric sensor may be incorporated into the identification appliance to monitor or detect the wearer's pulse rate, heart electrical signals, blood pressure, insulin levels, temperature and the like, where such biometric data may be transmitted to other devices (such as monitoring computers at a hospital) constantly, intermittantly, or upon alert conditions. The biometric sensor may be coupled to a data storage device, communication circuit, optical data display, or other components of the identification band. The biometric data may be encoded, converted into a data format according to a predetermined data template, and stored in a data storage device on the identification appliance. To verify the identity of the wearer of the identification appliance, any known method of comparing the stored biometric data and the wearer's biometric data may be used. For example, one method may be to determine the probability of a match. As an example of such a method, an XOR ("exclusive or") operation can be performed on the stored biometric data and the wearer's current biometric data to produce a third data set indicating those items in the first and second data sets that are not identical. A higher number of non-identical items will indicate a higher probability that the wearer is not the person whose encoded biometric data is stored in the identification band, and that number can also be compared to threshold numbers above which there are various predetermined levels of such probability (e.g. high, intermediate, or low). In accordance with corresponding biological features, data items can also be weighted in proportion to their effects on the overall certainty of identity verification. For instance, fingerprint data may be given higher weight than iris data. The results of the data comparison can also be displayed in a manner suitable for human judgment of probability.

Figure 8:
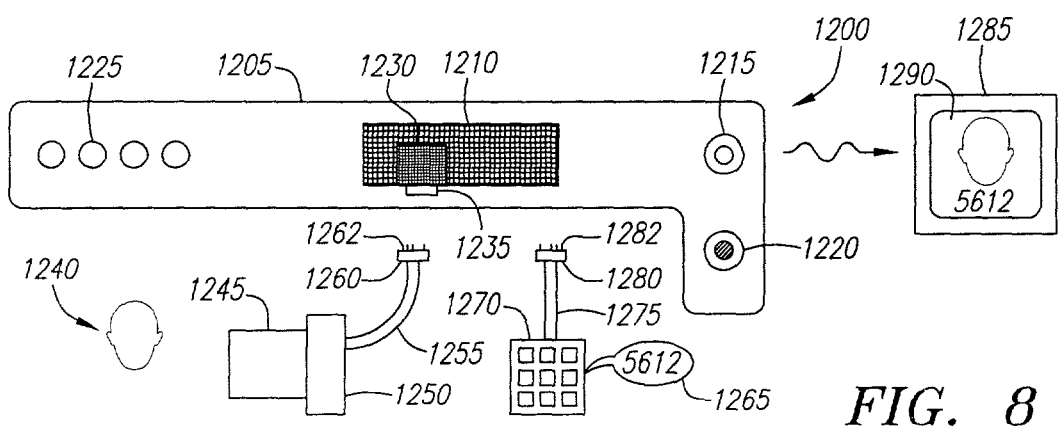
FIG. 8 is a representative illustration of another example embodiment of an improved identification band, which stores biometric and alphanumeric information.

FIG. 8 illustrates another example embodiment of an improved identification band 1200 in which biometric information and alphanumeric information are stored. As shown in FIG. 8, the improved band 1200 comprises a substrate 1205 having an RFID circuit 1210, a fastener with parts 1215 and 1220, adjusting holes 1225, a data storage device 1230 that is preferably a nonvolatile memory, and a jack 1235 for receiving encoded information to be stored in the data storage device 1230. A first set of receptacles within jack 1235 communicates with a first area in the data storage device 1230 that is reserved for biometric information, and a second set of receptacles communicates with a second area in the data storage device 1230 that is reserved for alphanumeric information. The jack 1235 may be configured to accept only one plug, or more than one plug, at a time.

As an example of the use of the improved band 1200 shown in FIG. 8, at the time of attachment of the band 1200 to a wearer 1240, the wearer 1240 is scanned by a charge-coupled device camera 1245 communicating with an encoder 1250 that converts the image signal to encoded image data and transmits that data through a first cable 1255, a first removable plug 1260 having pins 1262 that insert into the first set of receptacles within jack 1235, and into the area of the data storage device 1230 reserved for biometric information. Subsequently, the wearer 1240 enters a personal identification number ("PIN") 1265 shown in FIG. 8 as "5612" into keypad-encoder 1270 that converts the PIN sequence 1265 to encoded alphanumeric data and transmits that data through a second cable 1275, a second removable plug 1280 having pins 1282 that insert into the second set of receptacles within jack 1235, and into the area of the data storage device 1230 reserved for alphanumeric information. After attachment of the band 1200 to the wearer 1240, storage of the image and PIN data therein, and removal of plugs 1260 and 1280 from the jack 1235, the wearer is free to move around. To later ascertain or verify the identity of the wearer the image and PIN data are transmitted by the circuit 1210 to a reader 1285 such as a RFID reader, decoded and rendered into a viewable image and alphanumeric data on video screen 1290. The person, machine, or authorized agency making the verification can then compare the viewed image with the actual appearance of the wearer, and, for additional security, compare the viewed PIN to a PIN communicated by the wearer. Optionally, a signal may indicate whether the PINs matched. Alternatively to an electrical connection to a jack, an electromagnetically coupled circuit such as those used in a RFID tag may be used to transfer data. This method requires no physical contact with the circuitry of the identification band.

Figure 9:
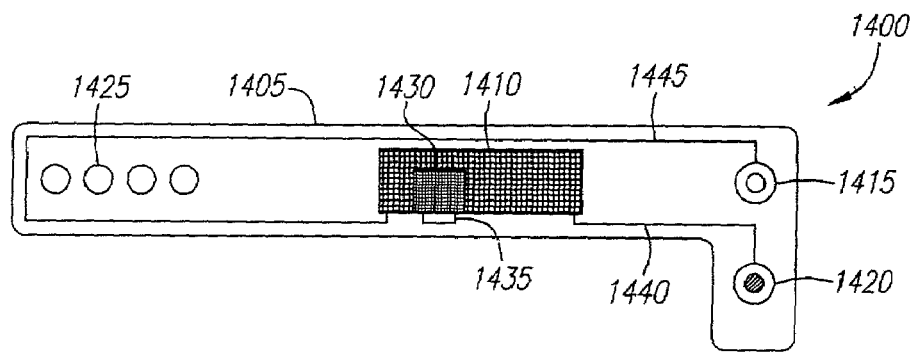
FIG. 9 is a representative illustration of an example embodiment of an improved identification band, which stores biometric and alphanumeric information and whose circuit functions are activated when the band is attached or deactivated when the band is unfastened, torn, cut, or overly stretched.

FIG. 9 is a representative illustration of an example embodiment of an improved identification band, which stores biometric and alphanumeric information and whose circuit functions are activated when the band is attached or deactivated when the band is unfastened, torn, cut, or overly stretched. As shown in FIG. 9, the improved band 1400 comprises a substrate 1405 having a circuit 1410, an electrically conductive fastener with parts 1415 and 1420, adjusting holes 1425, a data storage device 1430 that is preferably a nonvolatile memory in the circuit 1410 and a jack 1435 for receiving encoded biometric and alphanumeric information to be stored in the data storage device 1430. Alternatively, the data may be programmed into the data storage device of FIGS. 7–9 by electromagnetic coupling, such as through RF waves. Conductors 1440 and 1445 connect the circuit 1410 to each fastener part 1415 and 1420.

When the fastener closes, the parts 1415 and 1420 of the fastener come into contact, thereby closing the circuit through the conductors 1440 and 1445, enabling circuit functions, and making the stored data available for transmission by the circuit 1410. When the band 1400 is unfastened, or is torn, cut, or overly stretched and conductor 1440 or 1445 breaks, the circuit opens and disables any or all circuit functions. Optionally, the opening of the circuit may cause the circuit to alter or destroy any data stored in memory 1430. If the band 1400 is reattached, again closing the circuit through the conductors 1440 and 1445 and enabling circuit functions, the originally-stored data, having been altered, is no longer available for transmission.

Figure 10:
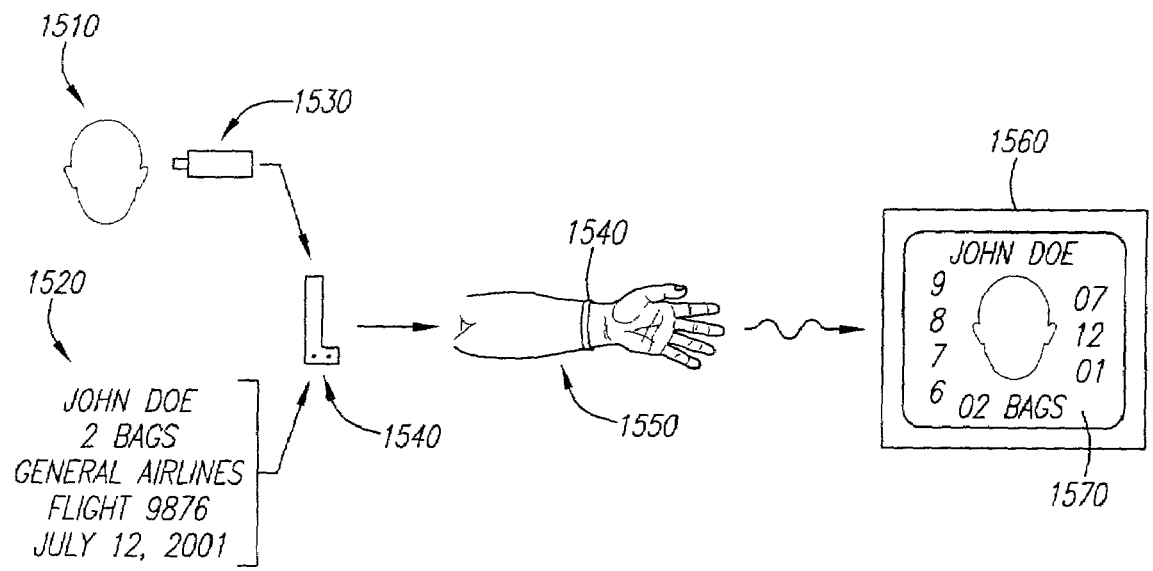
FIG. 10 is a representative illustration of an example method of using an improved identification band for passenger ticketing and boarding.

FIG. 10 is a representative illustration of an example method of using an improved identification band for passenger ticketing and boarding, such as at an airport, boat dock, train station, bus station and the like. As shown in FIG. 10, when a passenger 1510 checks in at a ticket counter, ticket information 1520 and, for example, an image of the passenger 1510 from a charge-coupled device camera 1530 and/or other identifying data are stored in a data storage device that is preferably a nonvolatile memory on the band 1540. The band 1540 is then attached to the wrist 1550 of the passenger 1510. Preferably, the band 1540 is the type in which the stored data is altered or destroyed when the band detects any tampering or detachment of the band. The band 1540 serves as a passenger ticket and boarding pass, and when the passenger 1510 is about to board, the stored data in the data storage device on the band 1540 on the wrist 1550 may be transmitted to a reader 1560, decoded and verified either automatically or by a human viewing data on a video screen 1570 so that the identity and proper ticketing of passenger 1510 can be verified.

Figure 11:
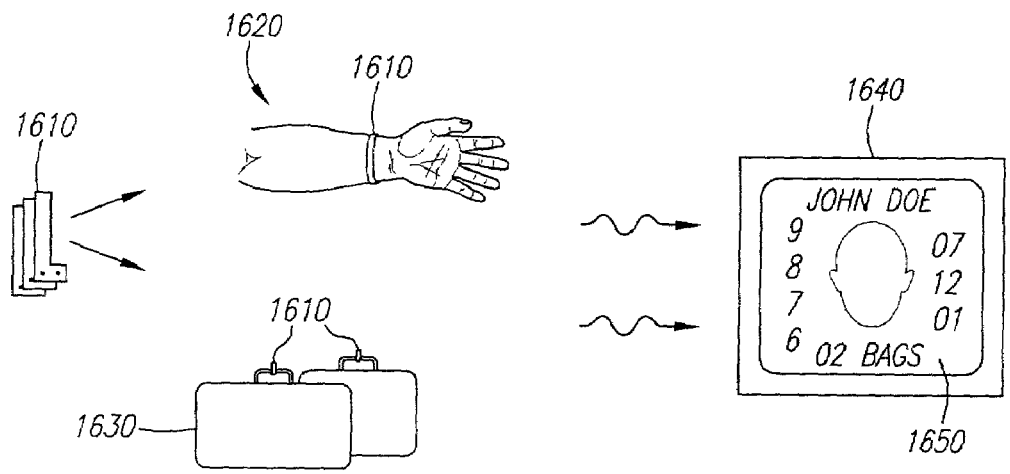
FIG. 11 is a representative illustration of an example method of using an improved identification band for passenger baggage tagging and claiming.

FIG. 11 is a representative illustration of an example method of using an improved identification band for passenger baggage tagging and claiming. At departure, identification bands 1610 are prepared with stored encoded passenger image or other identifying data and ticket information, one of which is attached to the passenger's wrist 1620 as a baggage claim receipt and the rest of which are attached to the passenger's baggage items 1630 as baggage tags. At the baggage claim in the destination terminal, the stored data in the identification bands 1610 on the wrist 1620 and on the baggage items 1630 are transmitted to a reader 1640, decoded and verified automatically or by a human viewing data on a video screen 1650, so that the baggage items 1630 can be properly claimed by matching the bands 1610 to each other.

Figure 12:
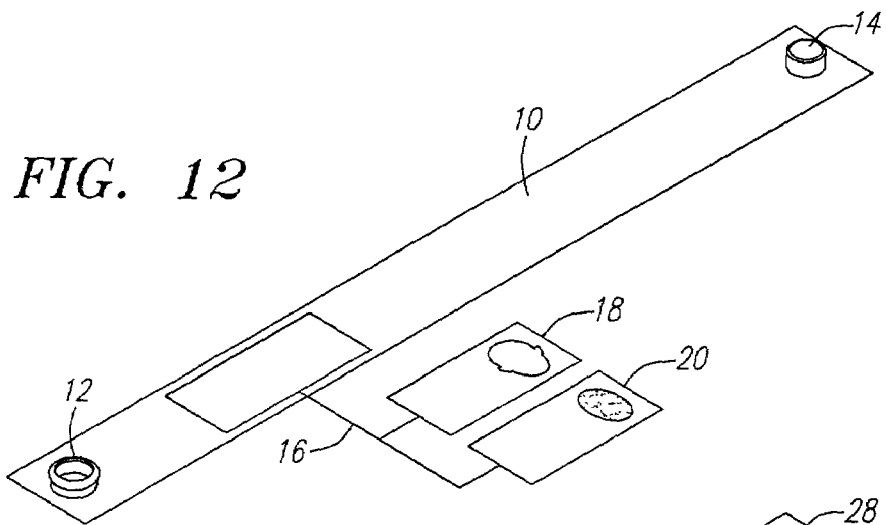
FIG. 12 is a representative illustration of an example embodiment of an improved identification appliance, such as an identification band, which has printed biometric-data.

FIG. 12 is a representative illustration of an example embodiment of an improved identification appliance, such as an identification band, which has printed biometric data. The example identification appliance has an elongate band 10, a band fastener 12, and a mating band fastener 14 that mates with the band fastener 12. The identification appliance can have printed information 16 and a portrait 18 or fingerprint 20.

Figure 13:
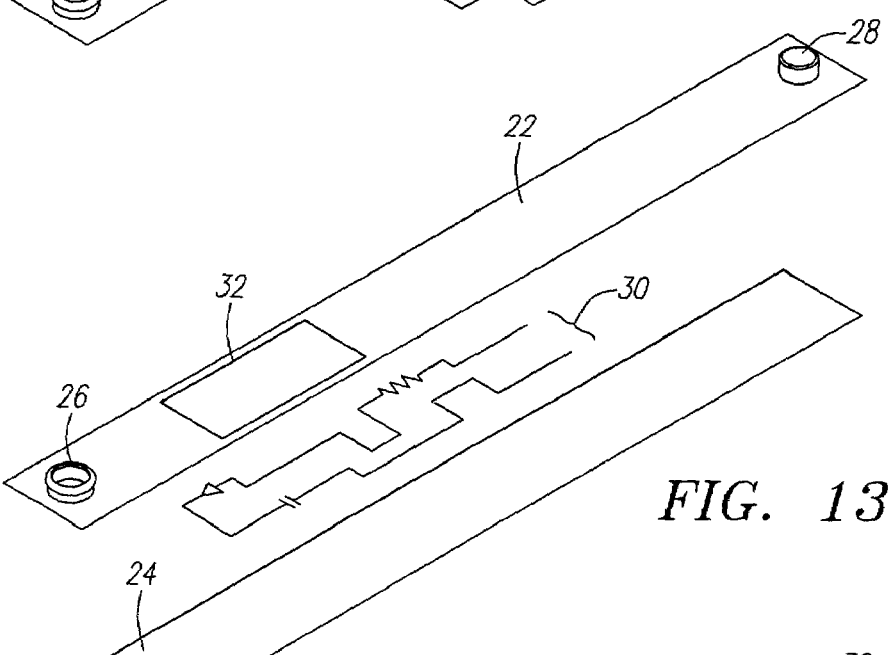
FIG. 13 is a representative illustration of another example embodiment of an improved identification appliance, such as an identification band, with printed biometric data.

FIG. 13 is a representative illustration of another example embodiment of an improved identification appliance, such as an identification band, with printed biometric data. The example identification appliance has an elongate band, a band fastener 26, and a mating band fastener 28 that mates with the band fastener 26. The elongate band may comprise a top laminate 22 and a bottom laminate 24. Silicon and/or printed circuitry components 30 may be sandwiched between the laminates 22, 24. The identification appliance may have printed biometric information 32 on any of its surfaces.

Figure 14:
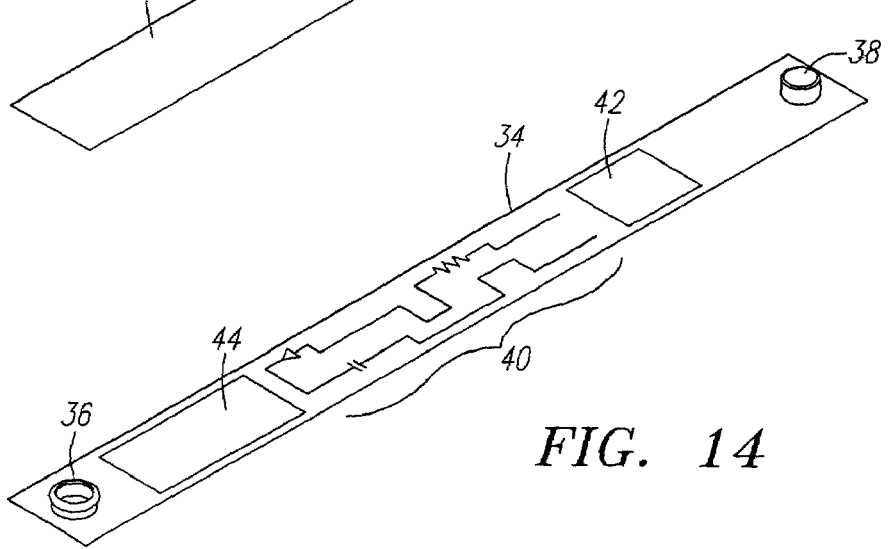
FIG. 14 is a representative illustration of an example embodiment of an improved identification appliance, such as an identification band, with a biometric sensor.

FIG. 14 is a representative illustration of an example embodiment of an improved identification appliance, such as an identification band, with a biometric sensor. The example identification appliance has an elongate band 34, a band fastener 36, and a mating band fastener 38 that mates with the band fastener 36. As with any of the embodiments described in this disclosure, silicon and/or printed circuitry components 40 may be embedded, printed, or otherwise deposited in or on the elongate band 34. The identification appliance may include a biometric sensor 42. The biometric sensor 42 may scan or otherwise obtain a person's fingerprint, iris, retina, or other identifying biometric feature and provide the biometric information to the circuitry 40. An example of such a biometric sensor built from an optical device is as follows. The optical device may include a layered structure containing a light emitting device(s) and semi-transparent light sensing devices for measuring light reflection of an object placed above the layered device. By using these optical devices, the reflective signature of a fingerprint could be illuminated, measured and recorded. The optical device may be a single device that senses the presence or absence of light wavelengths, the intensity of light wavelengths, or a time-varying optical signal carrying information. Alternatively, the optical device may comprise a plurality of sensing devices including a linear or two-dimensional array of sensors. The optical device may include a non-visible (i.e. infra-red or ultra-violet) optical input, optical output, or power conversion element. As with any of the described embodiments, the biometric sensor may be an optical sensor, a heat sensor, a pressure sensor, a humidity sensor, a chemical sensor, an electromagnetic sensor, or an acoustic sensor; the biometric sensor may be a plurality of devices that may be formed into a matrix (row/column addressable) or other spatially distributed pattern of elements. The circuitry 40 preferably includes other circuits, such as antenna circuitry, signal generator circuitry, communication circuitry, programmable encoder circuitry and interconnection circuitry, and is adapted to control and interact with the biometric sensor 42. The circuitry for the biometric sensor 42 may be made of silicon, organic materials, or other thin materials. Further, biometric information 44 may be printed on the band 34. The circuitry 40 may then compare the scanned biometric data with stored biometric data to determine their correlation. The identification appliance, as with any of the embodiments described in this disclosure, may include an audio, visual, or sensory (e.g., vibrating) device to indicate whether a correlation or match exists. As with any embodiment described in this disclosure, an optional antenna, electronic data storage device or memory, battery or power source, display, and/or printed biometric or alphanumeric information may be included as well.

Figure 15:
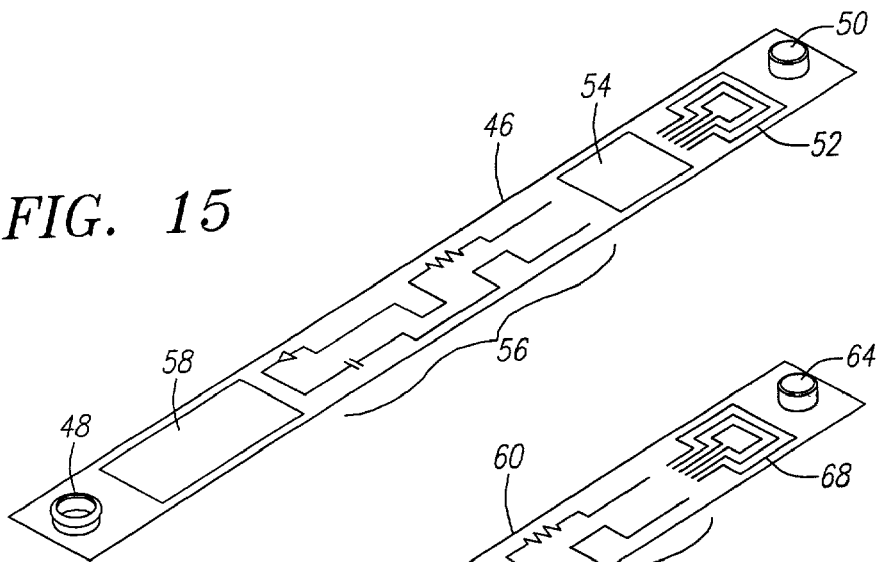
FIG. 15 is a representative illustration of another example embodiment of an improved identification appliance, such as an identification band, which has a biometric sensor and a wireless communication circuit.

FIG. 15 is a representative illustration of another example embodiment of an improved identification appliance, such as an identification band, which has a biometric sensor and a wireless communication circuit such as a REID circuit. The wireless communication circuit may incorporate any of the features, such as Bluetooth compatibility, described in concurrently filed U.S. patent application Ser. No. 10/101,471, filed Sep. 18, 2002, titled "Wearable Identification Appliance That Communicates With A Wireless Communication Network Such As Bluetooth," and subsequently published on Sep. 18, 2003 as U.S. Publication 2003/0174049, the entirety of which application is incorporated herein by reference for all purposes. The example identification appliance has an elongate band 46, a band fastener 48, a mating band fastener 50 that mates with the band fastener 48, silicon and/or printed circuitry components 56 that may be embedded or printed or otherwise deposited in or on the elongate band 46, a communication antenna 52 such as a RFID antenna that may be embedded or attached to the band 46, a biometric sensor 54, and printed biometric information 58 printed on the band 46. The biometric sensor 54, as with any of the embodiments in this disclosure, may scan a person's fingerprint, iris, retina, voice, or other identifying biometric feature. Of course, there may be more than one biometric sensor if desired. The biometric sensor 54 may be disposed in the elongate band 46, a securement structure used to fasten the identification band to a person, or both.

Figure 16:
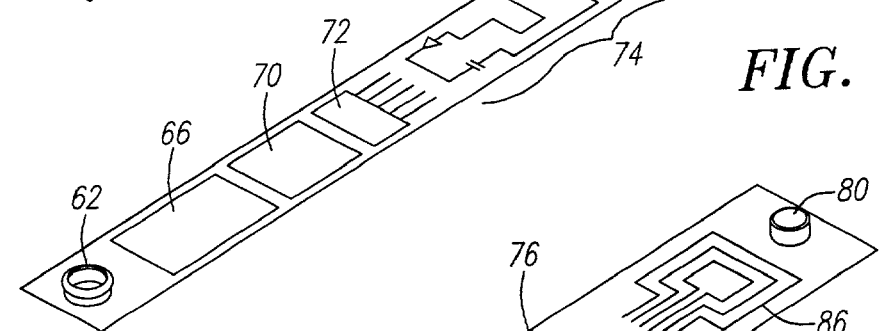
FIG. 16 is a representative illustration of an example embodiment of an improved identification appliance, such as an identification band, which has a biometric sensor, a wireless communication circuit such as a RFID circuit, and an electronic memory or data storage device.

FIG. 16 is a representative illustration of an example embodiment of an improved identification appliance, such as an identification band, which has a biometric sensor, a wireless communication circuit such as a RFID circuit, and an electronic memory or data storage device. The example identification appliance has an elongate band 60, a band fastener 62, a mating band fastener 64 that mates with the band fastener 62, silicon and/or printed circuitry components 74 that may be embedded or printed or otherwise deposited in or on the elongate band 60, a communication antenna 68 such as a RFID antenna that may be embedded or attached to the band 60, a biometric sensor 70, an electronic memory 72, and printed biometric information 66 printed on the band 60. The circuitry 74 preferably includes other circuits, such as antenna circuitry, signal generator circuitry, communication circuitry, programmable encoder circuitry and interconnection circuitry, and is adapted to control and interact with the biometric sensor 70 and electronic memory or data storage device 72. As with any embodiment described in this disclosure, the data storage device 72 may be any kind of memory or data storage device. The biometric sensor 70 may scan a person's fingerprint, iris, retina, voice, or other identifying biometric feature. Of course, there may be more than one biometric sensor if desired. The circuitry 74 may then compare the scanned biometric data with biometric data stored in the data storage device 72 to see if they match. The identification appliance may include an audio, visual, or sensory (e.g., vibrating) device to display the biometric data and/or to indicate whether a match exists, which device may optionally communicate the data remotely to a remote sensor or display device; such a display can be any of the displays described in this disclosure or known to those of skill in the art of displays.

Figure 17:
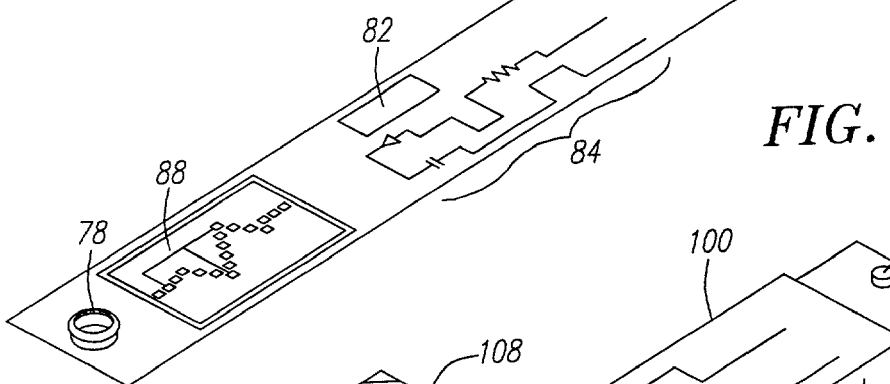
FIG. 17 is a representative illustration of yet another example embodiment of an improved identification appliance, such as an identification band, with a biometric sensor and display.

FIG. 17 is a representative illustration of yet another example embodiment of an improved identification appliance, such as an identification band, with a biometric sensor 82 and display 88. The identification appliance of FIG. 17 is similar to that of FIG. 16, except that FIG. 17 specifically illustrates a display 88. The example identification appliance has an elongate band 76, a band fastener 78, a mating band fastener 80 that mates with the band fastener 78, a communication antenna 86 such as a RFID antenna that may be embedded or attached to the band 76, and a biometric sensor 82. The identification appliance has silicon and/or printed circuitry components 84 that may be embedded, printed, or otherwise disposed in or on the elongate band 76 or its various layers. The biometric sensor 82 may sense or scan a person's fingerprint, iris, retina, voice, or other identifying biometric feature. The circuitry 84 may then compare the scanned biometric data with biometric data stored in the data storage device to determine if they match. The display 88 may display the biometric or other data and/or indicate whether a match exists in a manner perceptible to a person, such as by an audible, visual, or sensory (e.g., vibrating) device. An optional antenna, electronic data storage device or memory, acoustic sensor, chemical sensor, optical sensor, heat sensor, pressure sensor, humidity sensor, electromagnetic sensor, flexible keypad, battery or power source, and/or printed biometric or alphanumeric information may be included as well. As with any of the embodiments described in this disclosure, these optional devices and sensors may be disposed in the elongate band, a securement structure used to fasten the identification band to a person, or both.

Figure 18:
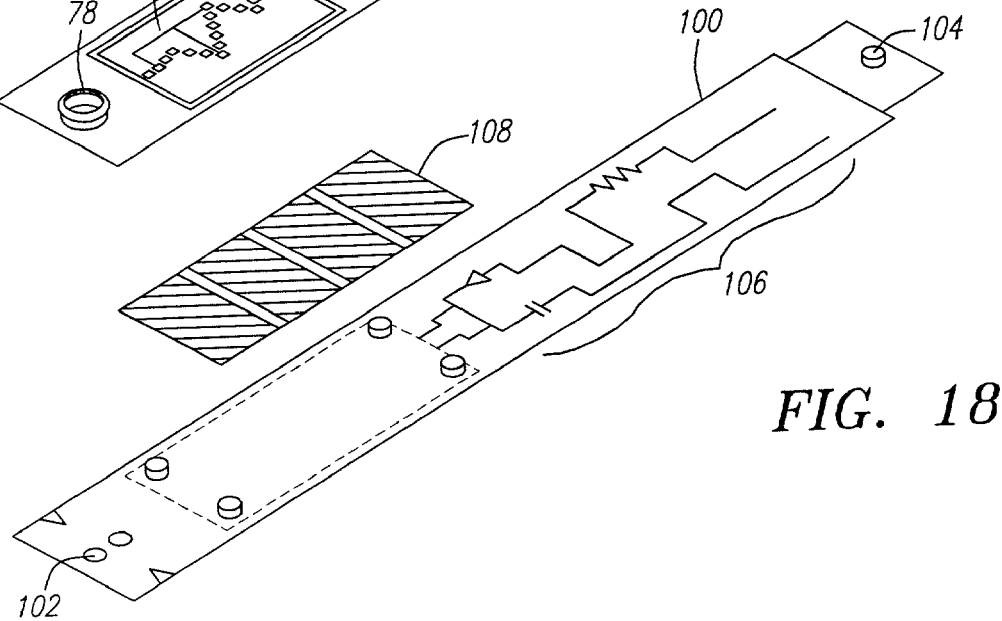
FIG. 18 is a representative illustration of an example embodiment of an improved identification appliance, such as an identification band, with photovoltaic cells.

FIG. 18 is a representative illustration of an example embodiment of an improved identification appliance, such as an identification band, with photovoltaic cells. The example identification appliance has an elongate band 100, a band fastener 102, a mating band fastener 104 that mates with the band fastener 102, silicon and/or printed circuitry components 106 that may be embedded or printed or otherwise deposited in or on the elongate band 100, and one or more photovoltaic cells 108. The photovoltaic cells 108 provide power, and optionally information such as a data signal from an optical source, to the circuitry 106. To generate photoelectric power, a photodiode (formed of silicon, amorphous silicon, or organic material) or photodiode array may be attached to or formed on the identification band. The photodiode could generate electric power to power the circuitry on the band, or recharge a battery attached to or formed in or on the band. The photodiode can also serve as a signal input transducer for information input to the identification band, which information may be transmitted to the identification band by a light source modulated by the information content. As with any embodiment described in this disclosure, an optional antenna, electronic data storage device or memory, biometric sensor, acoustic sensor, chemical sensor, optical sensor, heat sensor, pressure sensor, humidity sensor, electromagnetic sensor, flexible keypad, battery or power source, display, and/or printed biometric or alphanumeric information may be included as well.

Figure 19:
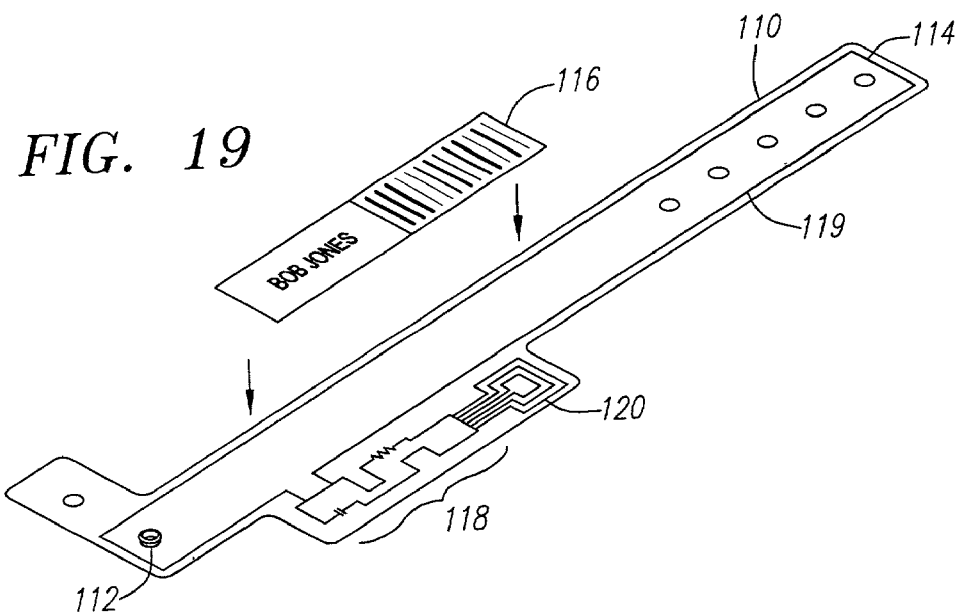
FIG. 19 is a representative illustration of an example embodiment of an improved identification appliance, such as an identification band, with embedded circuitry and a microstrip or patch antenna.

FIG. 19 is a representative illustration of an example embodiment of an improved identification appliance, such as an identification band, with embedded circuitry and a microstrip or patch antenna. The example identification appliance has an elongate band 110, a band fastener 112, a mating band fastener 114 that mates with the band fastener 112, silicon and/or printed circuitry components 118 that may be embedded or printed or otherwise deposited in or on the elongate band 110, printed biometric information 116, and a microstrip or patch antenna 120. A conductor or conductors 119 may span the length of the band 110 and be connected to the circuit 118, which conductors will break if the band is tampered with and optionally inform the circuit 118. The microstrip antenna 120 may be any of those described in co-pending patent application filed on Mar. 5, 2002, titled "Microstrip Antenna for Identification Appliance", U.S. patent application Ser. No. 10/101,471, and subsequently published on Sep. 11, 2003 as U.S. Publication 2003/0169207, the entirety of which application is incorporated by reference for all purposes. Such a microstrip antenna provides certain advantages, such as directing more of the radiating energy away from the wearer to improve the transmission range of the identification appliance and to reduce directing energy toward the wearer for health reasons. The microstrip antenna may be added or deleted from any of the embodiments described in this disclosure.

Figure 20:
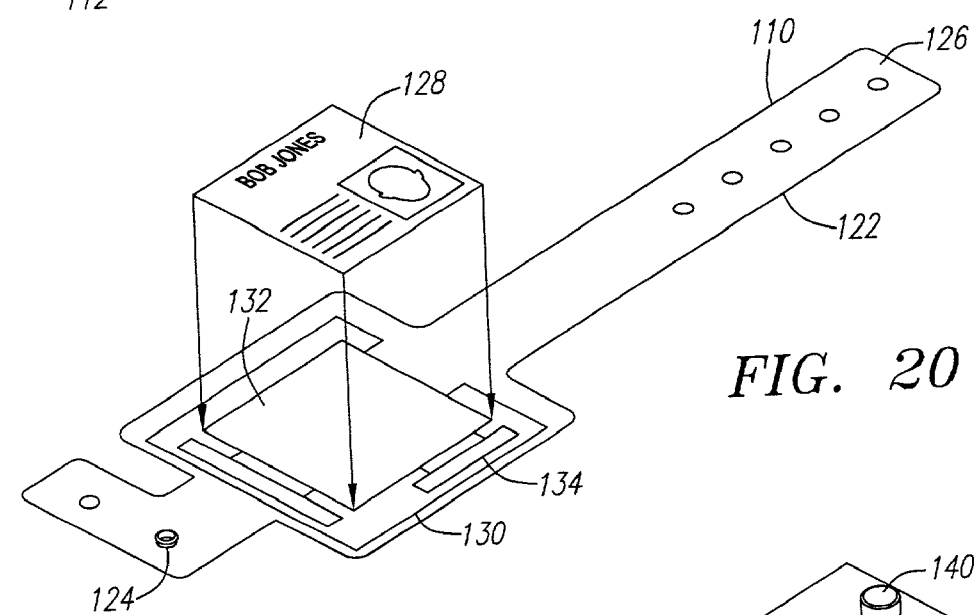
FIG. 20 is a representative illustration of an example embodiment of an improved identification appliance, such as an identification band, which performs signal processing and computation and has an electronic data storage device or memory.

FIG. 20 is a representative illustration of an example embodiment of an improved identification appliance, such as an identification band, which performs signal processing and computation and has an electronic data storage device or memory. The example identification appliance has an elongate band 122, a band fastener 124, a mating band fastener 126 that mates with the band fastener 124, silicon and/or printed circuitry components 132 that may be embedded or printed or otherwise deposited in or on the elongate band 122, printed biometric information 128, an antenna 130 and an electronic data storage device or memory 134. The circuitry 132 may include signal transmission circuitry, signal reception circuitry, data processing circuitry and computation circuitry, as desired. In this example, the circuitry 132, data storage device 134 and antenna 130 are sandwiched between the inner substrate of the body 122 and the structure carrying the printed information 128.

Figure 21:
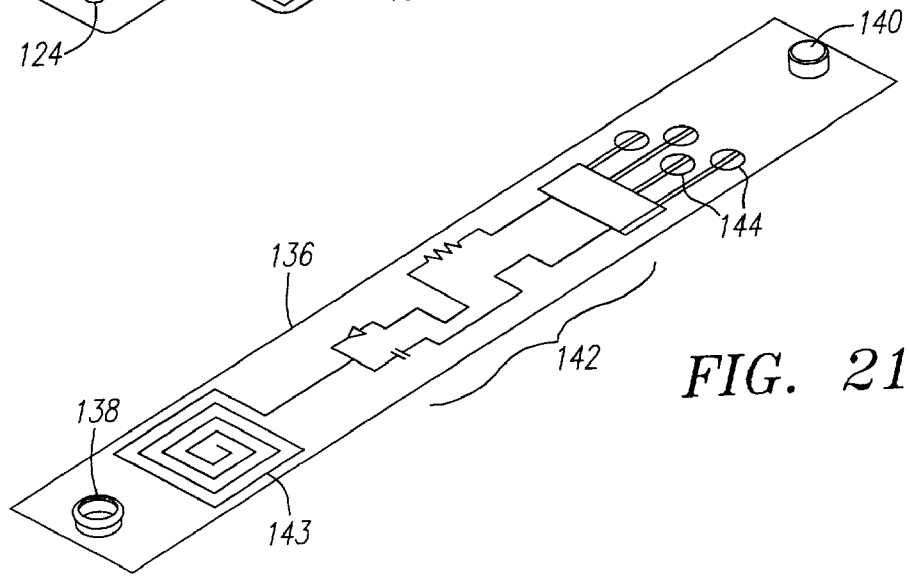
FIG. 21 is a representative illustration of an example embodiment of an improved identification appliance, such as an identification band, with one or more chemical sensors.

FIG. 21 is a representative illustration of an example embodiment of an improved identification appliance, such as an identification band, with one or more chemical sensors 144. The example identification appliance has an elongate band 136, a band fastener 138, a mating band fastener 140 that mates with the band fastener 138, silicon and/or printed circuitry components 142 that may be embedded or printed or otherwise deposited in or on the elongate band 136, and an antenna 143. Further, an optional antenna, electronic data storage device or memory, biometric sensor, acoustic sensor, optical sensor, heat sensor, pressure sensor, humidity sensor; electromagnetic sensor, flexible keypad, battery or power source, display, and/or printed biometric or alphanumeric information may be included. The chemical sensor may be any kind of chemical sensor. For example, it may sense physiological attributes of a person such as temperature, sweat content and pheromones.

Figure 22:
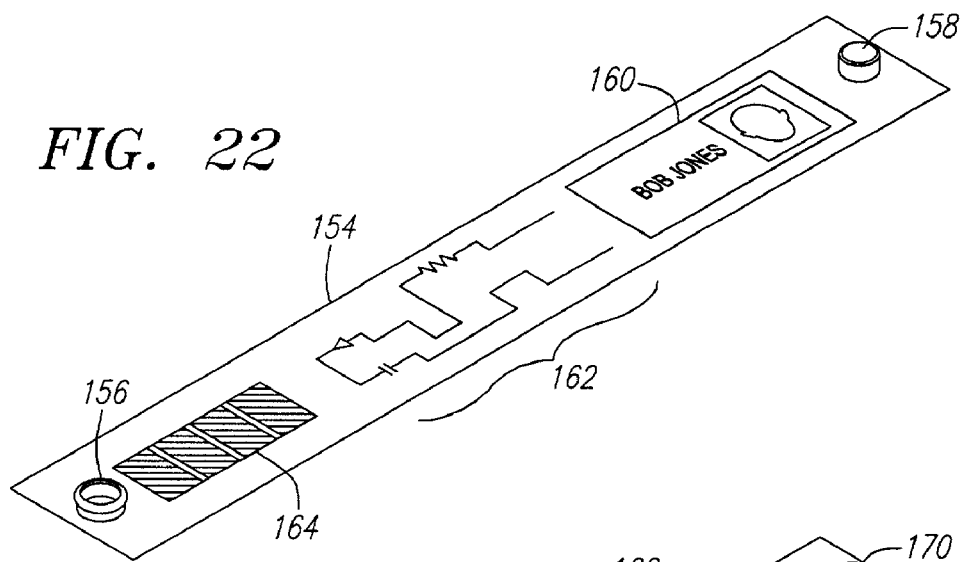
FIG. 22 is a representative illustration of an example embodiment of an improved identification appliance, such as an identification band, with an acoustic sensor.

FIG. 22 is a representative illustration of an example embodiment of an improved identification appliance, such as an identification band, with an acoustic transducer 164. Of course, a plurality of acoustic transducers may be provided, if desired. The acoustic sensors may comprise audio transducers for audio input or output. An audio signal such as speech from the wearer may be transduced and processed by known techniques and transmitted by the communication circuit in the identification appliance to a remote listener. Similarly, an audio signal may be received by the identification appliance from a remote transmitter by wireless communication, and processed and transduced to be audible to the wearer. The identification appliance also may have known algorithms to process speech recognition or output synthesized speech. The acoustic sensor 164 may comprise a piezoelectric transducer that detects acoustic waves. Other types of acoustic sensors may also be used. The acoustic information may be processed by a circuit 162, which may include any known voice activation or speech recognition algorithms. Further, the appliance may allow users to communicate two-way with remote units or have circuitry or algorithms to derive biometric data (such as a user's unique identifying speech patterns) from the user's speech. The example identification appliance has an elongate band 154, a band fastener 156, a mating band fastener 158 that mates with the band fastener 156, silicon and/or printed circuitry components 162 that may be embedded or printed or otherwise deposited in or on the elongate band 154, and printed biometric information 160. Further, an optional antenna, electronic data storage device or memory, biometric sensor, chemical sensor, optical sensor, flexible keypad, battery or power source, and/or display may be included as well.

Figure 23:
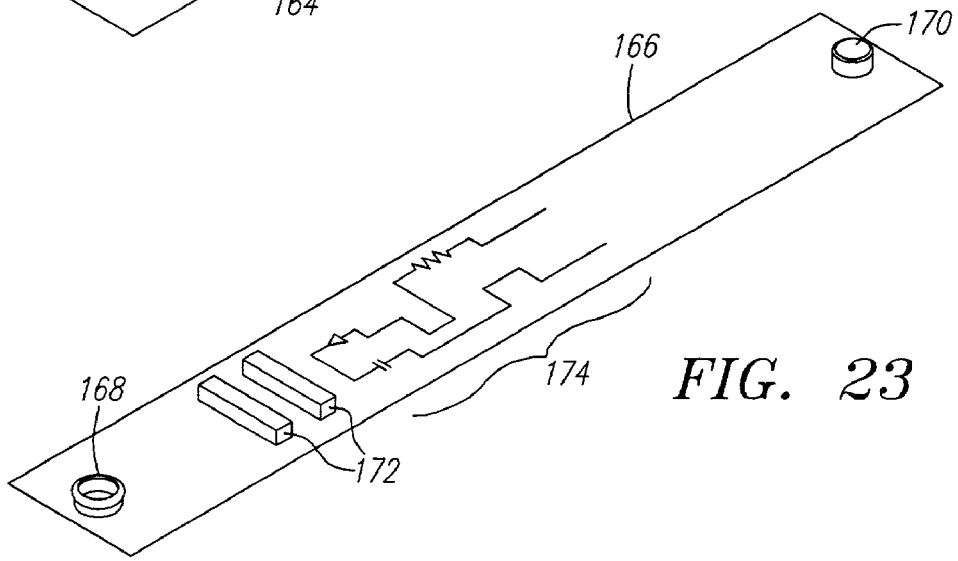
FIG. 23 is a representative illustration of an example embodiment of an improved identification appliance, such as an identification band, with electro-optical components.

FIG. 23 is a representative illustration of an example embodiment of an improved identification appliance, such as an identification band, with electro-optical or opto-electronic components 172. The example identification appliance has an elongate band 166, a band fastener 168, a mating band fastener 170 that mates with the band fastener 168, and silicon and/or printed circuitry components 174 that may be embedded or printed or otherwise deposited in or on the elongate band 166. The circuit 174 may control signals to or process signals from the electro-optical components 172. For example, the electro-optical components 172 may perform various functions such as communicating optically with an external or internal device, signaling (e.g., by light from a light emitting diode), indicating (e.g., by emitting light or varying light reflectances), displaying (e.g., of alphanumeric or image data by pre-formed indicators or matrix of indicators), sensing (e.g., of levels of light), and converting power (e.g., as a photovoltaic cell). As a further example, the electro-optical components 172 may comprise light emitting diodes (LEDs) that can be polymeric or organic LEDs as described in U.S. Pat. No. 5,973,598. If the electro-optical components 172 perform an optical communication function, they may include optical fibers, light sources and/or light detectors such as photodetectors. If desired, the electro-optical components 172 may act as an electro-optical display device by including liquid crystal displays, electrophoretic displays, gas discharge displays and electromechanical displays. If desired, the electro-optical components 172 may include an electro-optical input device by including photodiodes, photoresistors, photomultiplier tubes and other input devices. The electro-optical components 172 may be of silicon or other materials, while some electro-optical components 172 may be fabricated partially or predominantly of organic compounds. They may be inflexible and attached on the identification appliance. Alternatively, they may be flexible and attached to or printed on the identification band. The electronic, electro-optical and visual components may be printed or otherwise deposited on the identification appliance's elongate structure (e.g., 91 in FIG. 2, 10 in FIG. 12).

Figure 24:
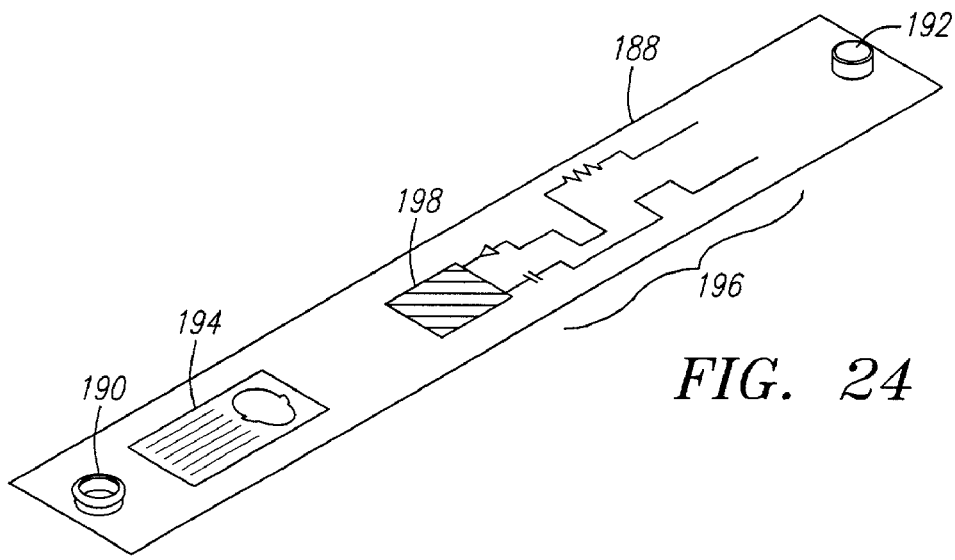
FIG. 24 is a representative illustration of yet another example embodiment of an improved identification appliance, such as an identification band, with an optical sensor.

FIG. 24 is a representative illustration of yet another example embodiment of an improved identification appliance, such as an identification band, with an optical sensor 198. The example identification appliance has an elongate band 188, a band fastener 190, a mating band fastener 192 that mates with the band fastener 190, printed information 194, and silicon and/or printed circuitry components 196 that may be embedded or printed or otherwise deposited in or on the elongate band 188. The circuit 196 may control the optical sensor 198. For example, the optical sensor 198 may perform optical communication with an external or internal device. The optical sensor 198 may comprise a light detector such as a photodetector, or a charge coupled device to capture images of, for example, a person's face, fingerprint, iris, or retina.

Figure 25:
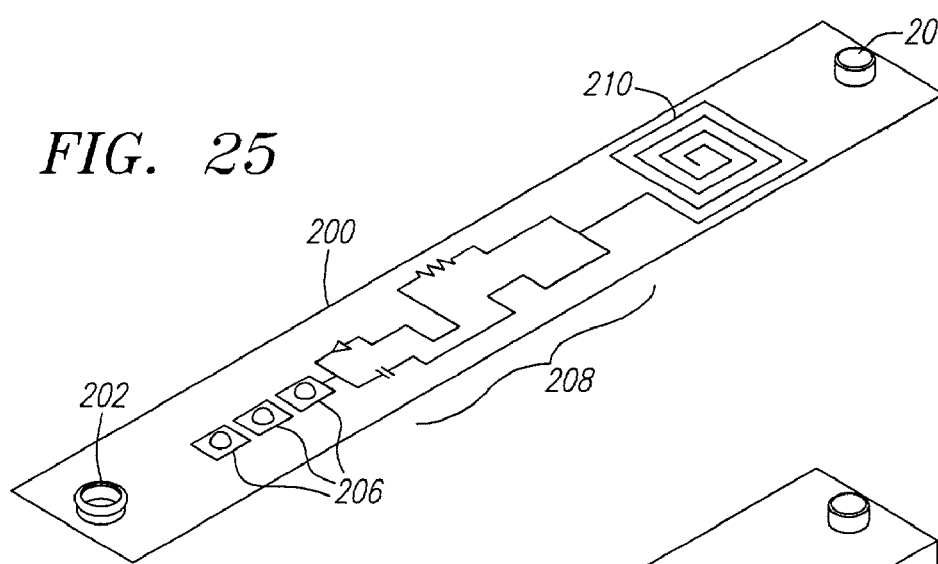
FIG. 25 is a representative illustration of an example embodiment of an improved identification appliance, such as an identification band, with a flexible keypad.

FIG. 25 is a representative illustration of an example embodiment of an improved identification appliance, such as an identification band, with a flexible keypad 206. The example identification appliance has an elongate band 200, a band fastener 202, a mating band fastener 204 that mates with the band fastener 202, silicon and/or printed circuitry components 208 that maybe embedded or printed or otherwise deposited in or on the elongate band 200, and an antenna 210. The circuit 208 may control the keypad 206. Of course, the keypad 206 may comprise a full typewriter keyboard, a partial keyboard, a single key, or a plurality of custom function keys. The keypad 206 permits users to input data into the circuit 208 or an optional data storage device. The keypad may be based on symbolic or alpha-numeric data.

Figure 26A:
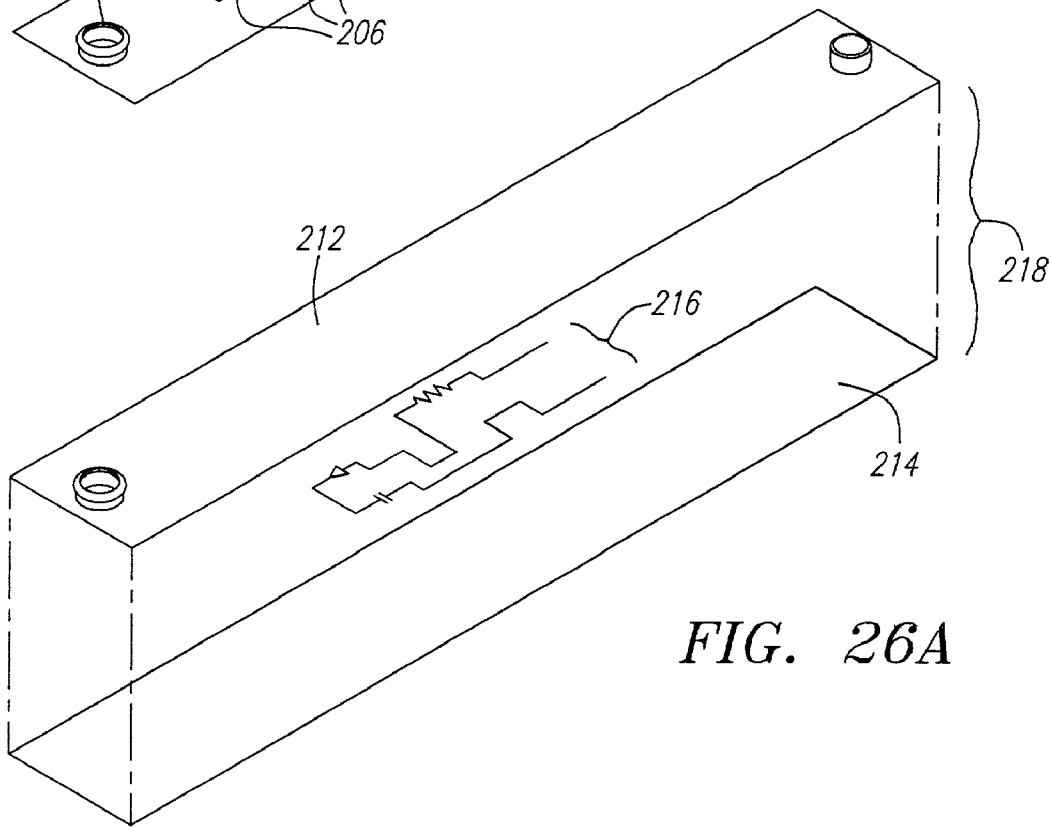
FIGS. 26A and 26B are representative illustrations of an example method of embedding silicon and/or printed circuitry, or other components, in an identification appliance such as an identification band.
Figure 26B:
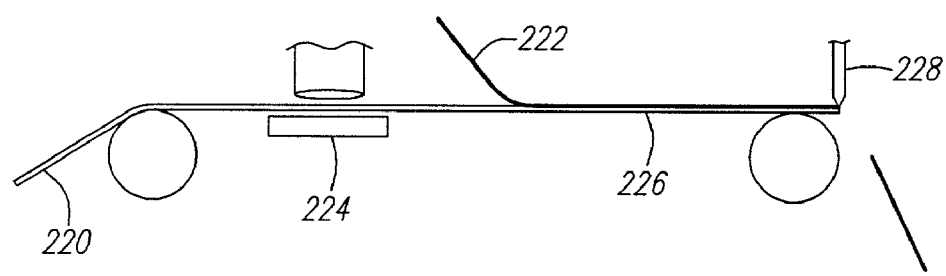

FIGS. 26A and 26B are representative illustrations of an example method of embedding silicon and/or printed circuitry, or other components, in an identification appliance such as an identification band. A top laminate 212 and a bottom laminate 214 may be adhered to each other. As shown by reference numeral 218, silicon and/or printed circuitry 216 and other components may be formed or printed on either the top or bottom laminates 212, 214, or both laminates, and additional components may be sandwiched between the top and bottom laminates 212, 214. A manufacturing assembly is illustrated in FIG. 26B. The bottom laminate material 214 is fed at 220 and a machine 224 adheres circuitry 216 and other components to the bottom laminate 214. The top laminate material 214 is fed at reference numeral 222 and joined to the bottom laminate 218 by laminating machine 226. A cutting device 228 separates the joined material into separate identification appliances. Of course, in any of the manufacturing processes described in this disclosure, other manufacturing steps known to those of skill in the art of making identification appliances may be used as desired.

Figure 27A:
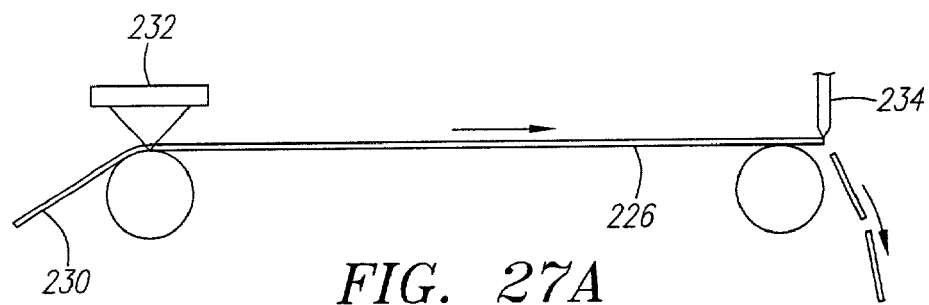
FIGS. 27A and 27B are representative illustrations of an example method of implementing printed circuitry in an identification appliance such as an identification band.
Figure 27B:
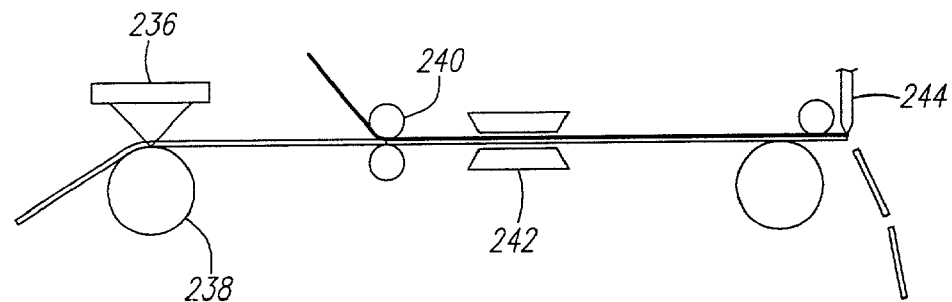

FIGS. 27A and 27B are representative illustrations of an example method of implementing printed circuitry in an identification appliance such as an identification band. The body material is fed at 230 and a machine 232 prints or deposits circuitry and other components onto the body material. The machine may be an ink jet printing device, stencil, or any other method of imprinting inks or materials on a substrate. A cutting device 234 separates the body material into separate identification appliances. In FIG. 27B, a bottom laminate material is fed at 238 and a machine 236 prints or otherwise deposits circuitry and other components onto the bottom laminate. The top laminate material is fed at reference numeral 240 and joined to the bottom laminate by laminating machine 242. A cutting device 244 separates the joined material into separate identification appliances. Of course, other manufacturing processes known to those of skill in the art of making identification appliances may also be used as desired.

Figure 28:
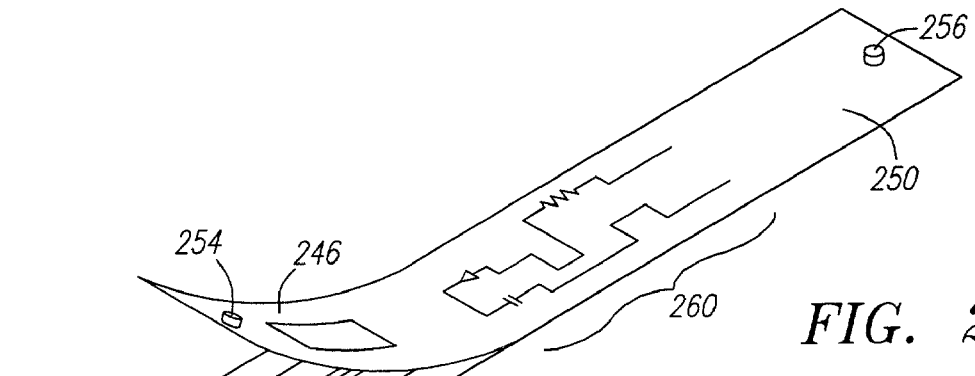
FIG. 28 is a representative illustration of an example embodiment of an improved identification appliance, such as an identification band, with a flexible battery or power source.

FIG. 28 is a representative illustration of an example embodiment of an improved identification appliance, such as an identification band, with a flexible battery or power source 258. In this particular example, the identification appliance has an elongate band formed out of a top laminate 246 and a bottom laminate 248. A band fastener 252 mates with another band fastener 256. Silicon and/or printed circuitry components 260 also may be embedded or printed or otherwise deposited in or between the laminated band. The flexible battery 258 powers the circuit 260 as well as any other component on the identification appliance requiring power. Such other components may include, for example, an electronic data storage device or memory, biometric sensor, acoustic sensor, chemical sensor, optical sensor, flexible keypad and display. Preferably, the battery 258 is thin and flexible. The battery 258 may provide primary or auxiliary power for electronic circuits. Optionally, the battery 258 may include a photovoltaic component so that the battery is charged or recharged by ambient light; the photovoltaic cells and recharging circuitry can be formed out of inorganic or organic materials. The battery 258 may be replaceable or not. The battery 258 may be a flexible polymer battery imprinted on or constructed on the identification appliance substrate, as described in U.S. Pat. No. 5,973,598. The battery 258 may be activated when the identification appliance is fastened to its object, or activated by the reception of an optical signal or an electromagnetic signal. An identification appliance with a battery 258 may be activated upon proper authorization or the start of service.

Figure 29:
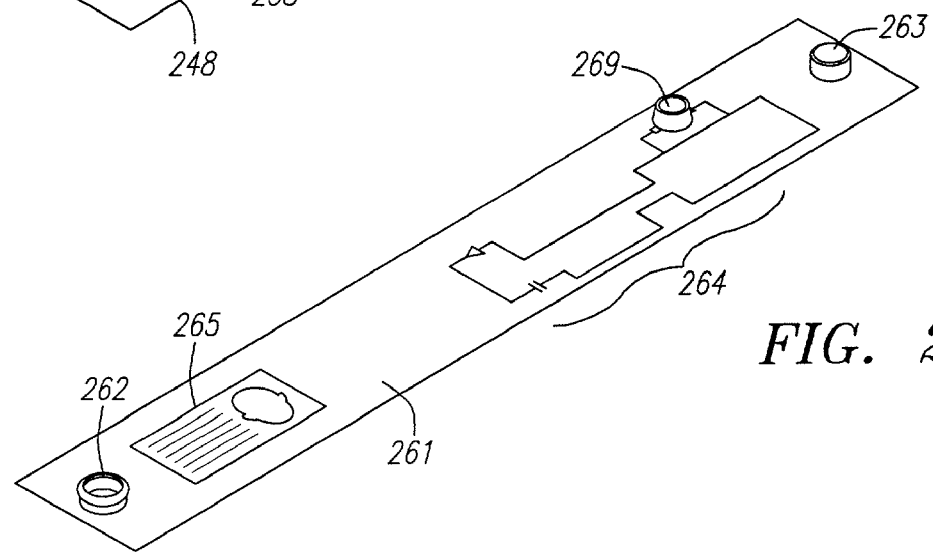
FIG. 29 is a representative illustration of another example embodiment of an improved identification appliance, such as an identification band, with a "button" style battery.

FIG. 29 is a representative illustration of another example embodiment of an improved identification appliance, such as an identification band, with a "button" style battery 269. The example identification appliance has an elongate band 261, a band fastener 262, a mating band fastener 263 that mates with the band fastener 262, silicon and/or printed circuitry components 264 that may be embedded or printed or otherwise deposited in or on the elongate band 261, and printed information 265. The battery 269 is a button-style battery in this example embodiment. The battery 269 powers the circuit 264 as well as any other component on the identification appliance requiring power. Such other components may include, for example, an electronic data storage device or memory, biometric sensor, acoustic sensor, chemical sensor, optical sensor, flexible keypad and display. Preferably, the battery 269 is small and thin. The battery 269 may provide primary or auxiliary power for electronic circuits. The battery 269 is replaceable.

Figure 30:
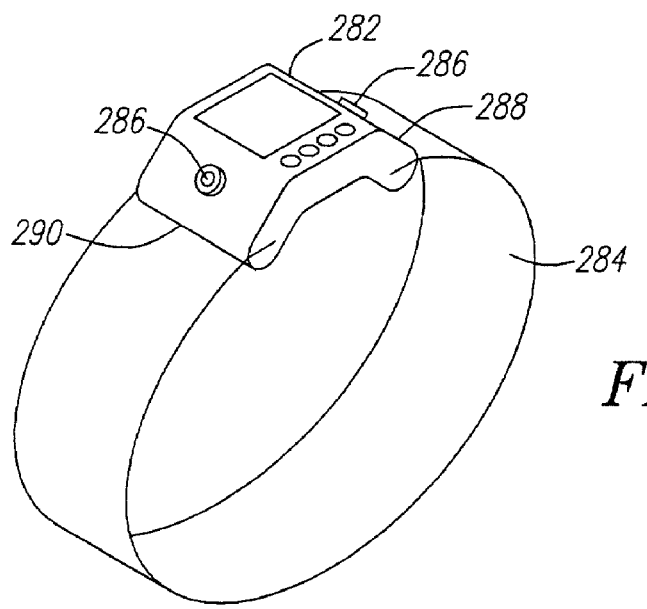
FIG. 30 is a representative illustration of an example embodiment of an improved identification appliance, such as an identification band, which is partially disposable.

Any of the identification appliance embodiments described in this disclosure may be completely disposable, partially disposable, or reusuable. The disposable identification appliance may incorporate any of the functions described in this disclosure, where the fastening means is not re-usable and the functionality of the identification appliance is destroyed after its use. The identification appliance may have a disposable section (for example, the band) and a re-usable section (for example, the circuit). The identification appliance also may be made water resistant, waterproof, and/or resistant to certain solvents or chemicals used in the area of its application. If disposable, the band or body is preferably made of an inexpensive material such as paper, plastic, or other laminate material. For example, FIG. 30 is a representative illustration of an example embodiment of an improved identification appliance, such as an identification band, that is partially disposable. An example of a partially disposable identification band is described in U.S. patent application Ser. No. 09/033,832, which is titled "Identification Device Having Reusable Transponder" and is published as PCT US98/04098. The identification appliance comprises a disposable band 284 and a non-disposable "hub" 282 of circuitry, sensors and other circuit components. The band 284 is fastened by inserting one end 288 of the band to the non-disposable hub 282, which attachment is made more secure by a fastener 286, and by inserting the other end 290 of the band to the non-disposable hub 282, which attachment is made more secure by a fastener 286. When desired, the disposable band 284 may be unfastened from the non-disposable hub 282 and disposed. A replacement band may be fastened to the non-disposable hub 282. If the replacement band is for a different user, any data stored in the non-disposable hub 282 may be erased and updated.

Figure 31:
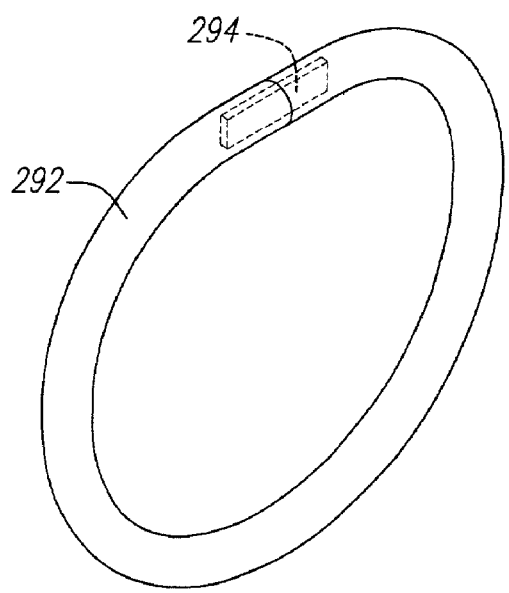
FIG. 31 is a representative illustration of another example embodiment of an improved identification appliance, such as an identification band, which is partially disposable.

FIG. 31 is a representative illustration of yet another example embodiment of an improved identification-appliance that is partially disposable. . The identification appliance comprises a disposable flexible plastic or rubber tube 292, which acts as a band and houses an insertable and reusable circuit portion 294. The circuit portion 294 may include any kind of circuits such as communication circuitry and biometric circuitry.

Figure 32:
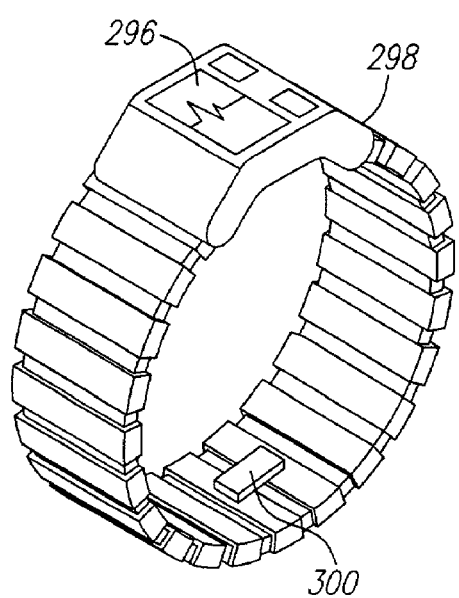
FIG. 32 is a representative illustration of an example embodiment of an improved identification appliance that is reusable.

FIG. 32 is a representative illustration of an example embodiment of an improved identification appliance that is reusable. This example identification appliance comprises a non-disposable band 298, which may be decorative to resemble jewelry or a watch. In or on the band 298 is placed non-disposable circuitry, sensors and components 296. An optional lock mechanism 300 may be provided to secure the identification appliance to a wearer and to allow the wearer to adjust its size. The lock mechanism may be activated or inactivated either by the wearer or alternatively by the person or agency responsible for providing the security function performed by the identification appliance. The locking may be mechanical or electromechanical. The locking or un-locking function may be performed by remote communication or control, if desired.

Figure 33A:
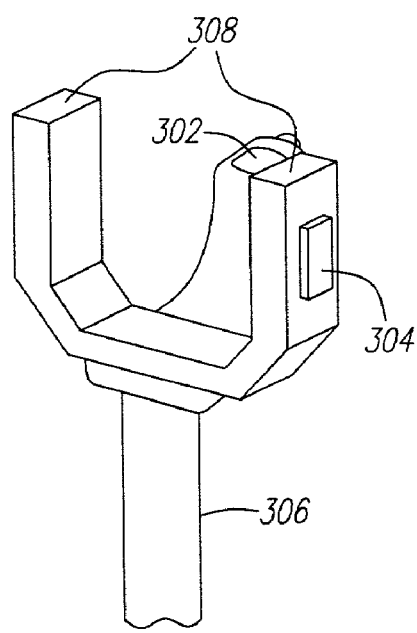
FIGS. 33A, 33B and 33C are representative illustrations of example embodiments of a biometric reader/verifier of identification appliances.
Figure 33B:
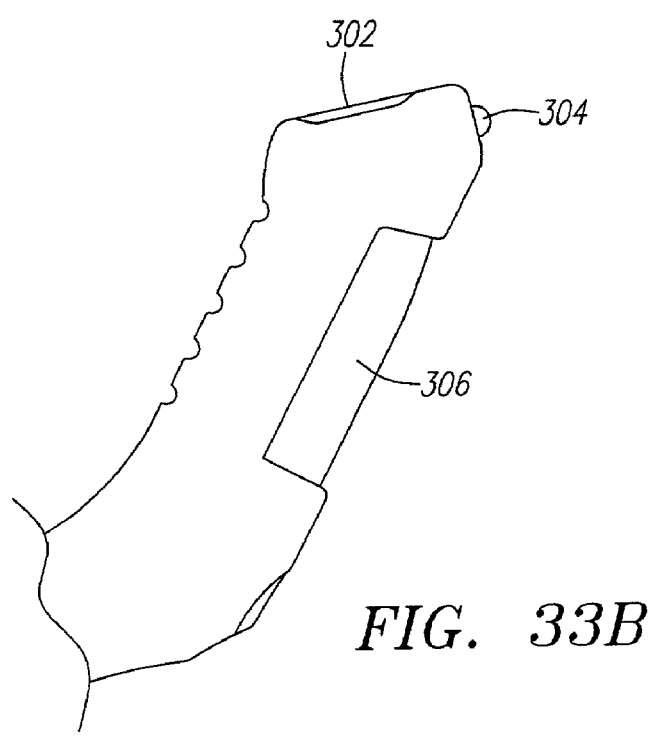
Figure 33C:
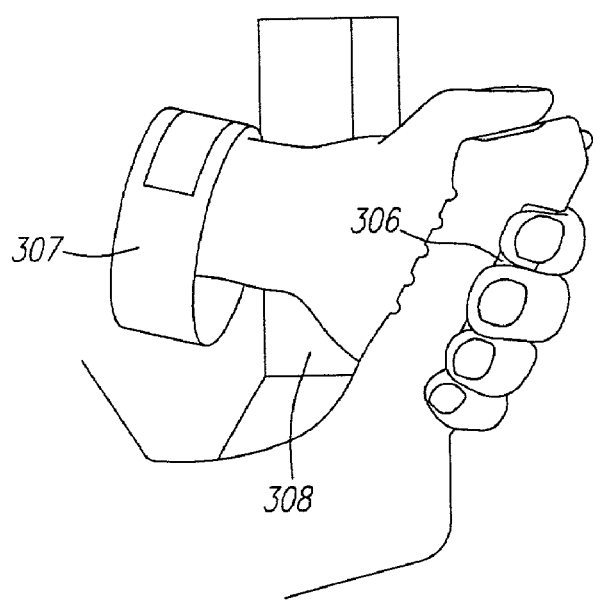

FIGS. 33A, 33B and 33C are representative illustrations of example embodiments of a biometric reader/verifier of identification appliances. Referring to FIG. 33A, a biometric sensor 302 is mounted on a grip 306. The biometric sensor 302 may be any of the biometric sensors known to those of skill in the art of biometrics and those described in this disclosure. An interrogator 308 communicates, such as by radio frequency, to the identification appliance in order to obtain the biometric data stored in the appliance. An optional indicator or alarm system 304 may provide an audible, visible, or other perceptible indication as to, for example, whether the biometric data obtained by the biometric reader/verifier matches the biometric data stored in an identification appliance. Turning to FIG. 33B, the grip 306 may have a biometric sensor 302 and indicator 304 built into the handle of the grip. FIG. 33C is a representative illustration of a wearer of an identification appliance using an example embodiment of a reader/verifier. The user grasps the grip 306, thereby positioning the identification appliance 307 within range of the interrogator 308. The interrogator 308 communicates, such as by radio frequency, with the identification appliance 307 in order to obtain the biometric data and/or other data stored in the appliance.

Figure 34A:
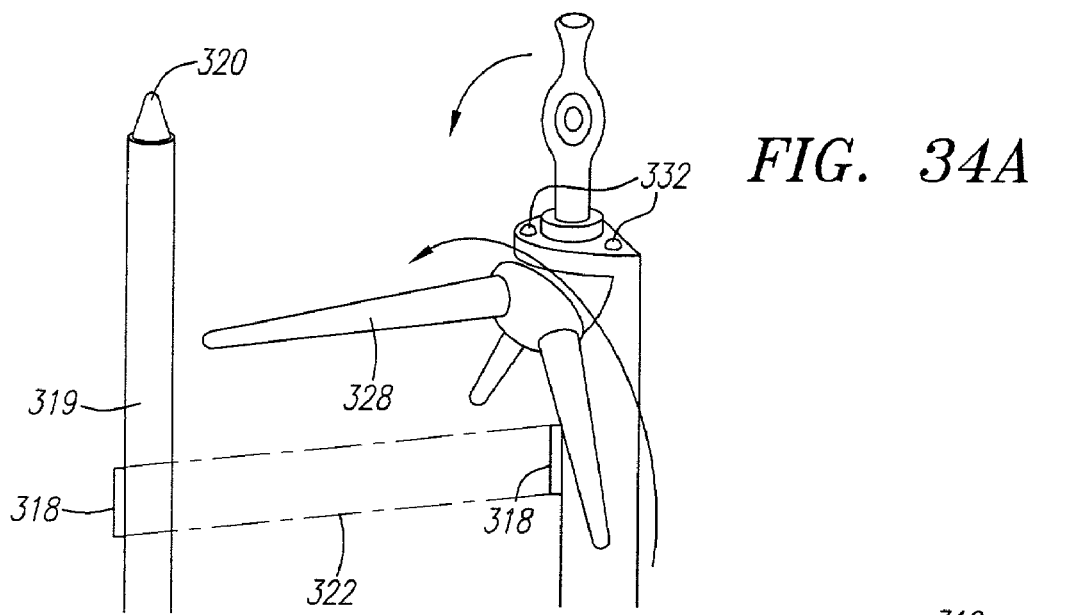
FIGS. 34A, 34B and 34C are representative illustrations of example applications of a biometric identification appliance reader/verifier.
Figure 34B:
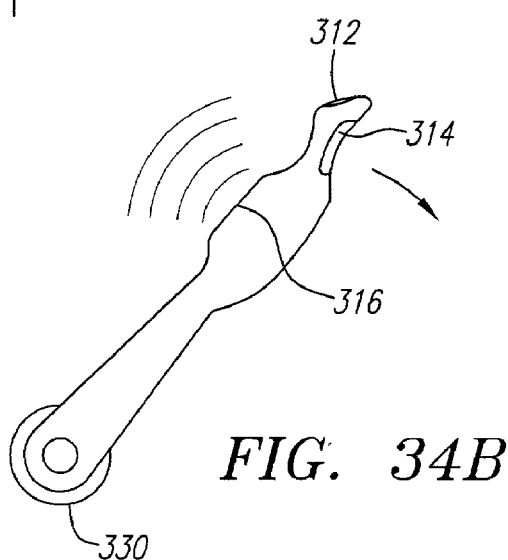
Figure 34C:
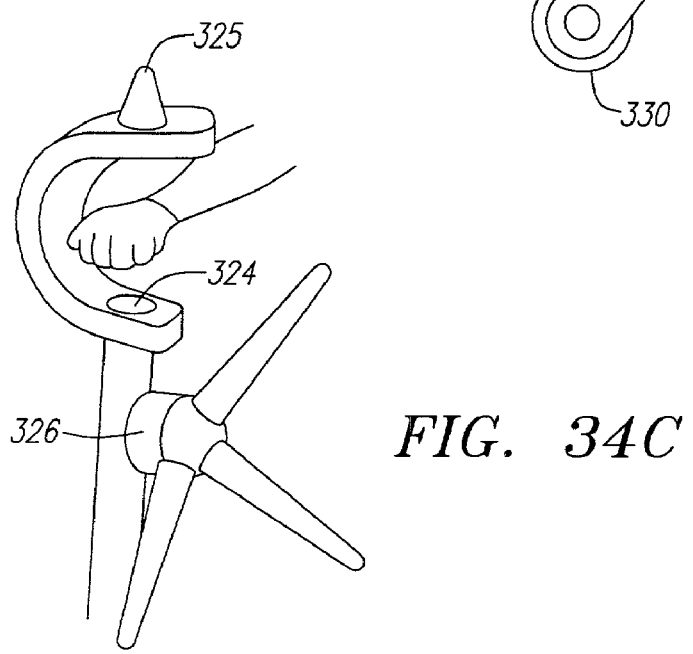

FIGS. 34A, 34B and 34C are representative illustrations of example applications of a biometric identification appliance reader/verifier. In particular, FIG. 534A is a representative illustration of an example embodiment of a biometric turnstile system. The turnstile system allows authorized personnel to pass between the turnstile arm 328 and a post 319. Device 318 may emit beams 322 that are used to detect whether anyone is at the turnstile arm, or trying to go under the turnstile arm 328. The device 318 may include a reader/verifier of identification appliances. When a person wearing an identification appliance approaches the turnstile arm 328, the beams 322 detect the person and read identifying information, such as biometric data, from the identification appliance. If the identifying information gives the wearer the privilege or authority to pass, the turnstile arm 328 may be rotated out of the way to permit the wearer to pass. If, however, the wearer lacks the privilege to pass, an optional visible alarm system 320 and/or audible alarm system 332 may indicate that an unauthorized person is present.

FIG. 34B is a representative illustration of the details of an alternative biometric turnstile arm that may be used in FIG. 34A. The turnstile arm comprises a biometric sensor 312, a grip 314 with an optional built in biometric sensor and an interrogator 316. The turnstile arm has an axis 330 of rotation. The biometric sensor 312 may be any of the biometric sensors known to those of skill in the art of biometrics and those described in this disclosure. The interrogator 316 communicates, such as by radio frequency, to the identification appliance in order to obtain identifying biometric data stored in the appliance. An optional indicator or alarm system may provide an audible, visible, or other perceptible indication as to, for example, whether the biometric data obtained by the biometric sensor 312 matches the stored biometric data obtained from the identification appliance.

FIG. 34C is a representative illustration of another example embodiment of an biometric gate. A turnstile 326 prevents people from entering a restricted area, such as a secure area or an amusement park. The turnstile includes a curved interrogator 324, which in the alternative, may have any suitable shape for reading a person's identification appliance. In the example illustrated in FIG. 34C, a person wanting to gain access inserts his identification appliance, such as an identification wristband, into the vicinity of the interrogator 324. The interrogator 324 communicates, such as by radio frequency, to the identification appliance in order to obtain identifying biometric data stored in the appliance. The turnstile may include an biometric sensor 325 that obtains the person's biometric data (e.g., fingerprint, iris, retina scan). The interrogator 324 compares the person's biometric data from the biometric sensor 325 and compares the data to the biometric data obtained from the identification appliance. An optional indicator or alarm system may provide an audible, visible, or other perceptible indication as to whether there is a match or non-match of biometric data.

Figure 35:
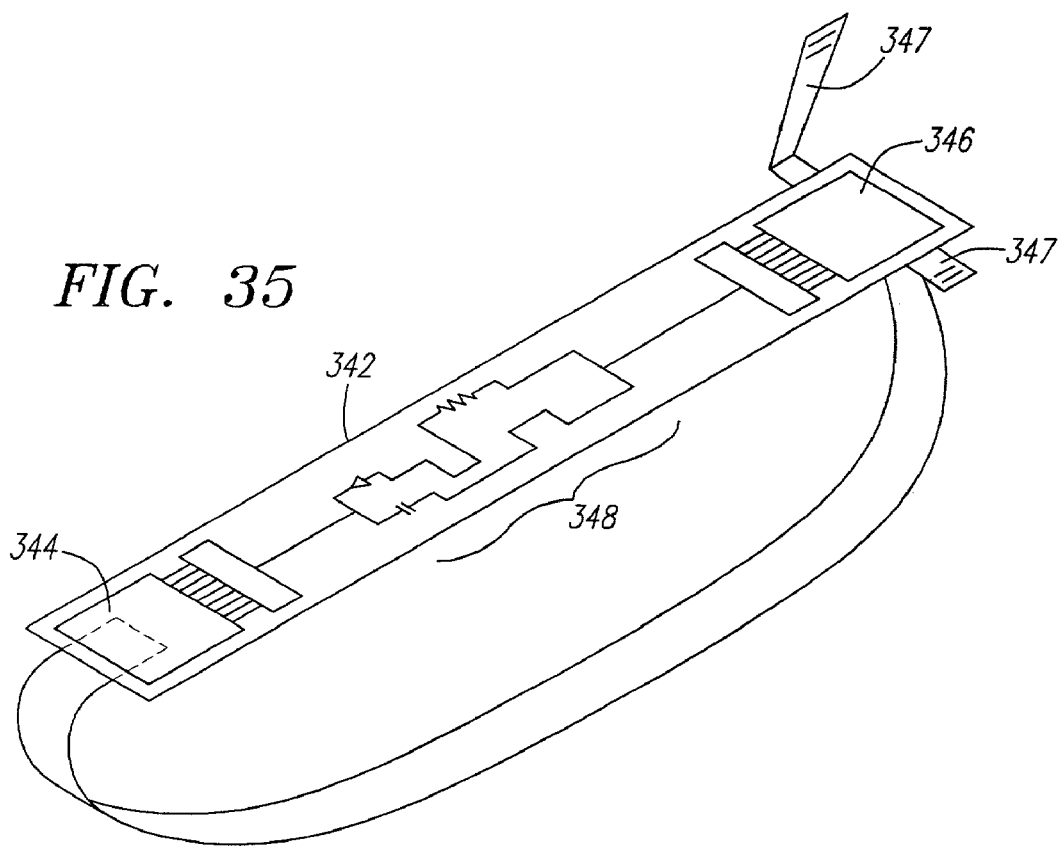
FIG. 35 is a representative illustration of an example embodiment of an improved secure identification appliance, such as an identification band, with electronic tamper detection.

FIG. 35 is a representative illustration of an example embodiment of an improved secure identification appliance, such as an identification band, with electronic tamper detection. The example identification appliance has an elongate body 342, a first patch of a plurality of conductive contacts 344, a second patch of a plurality of conductive contacts 346 and a securing device 347. When the securing device 347 is closed (to fasten the identification appliance to a wearer), a physical and electrical contact is formed between contacts 344 and 346. The groups of contacts 344, 346 may be formed in patterns such that when the identification appliance is secured by device 347, the resulting pattern of closed electrical contacts may be random or unpredictable. Circuitry 348 that may be embedded, printed, deposited, or otherwise placed in or on the band 342 monitors whether the electrical contact is open or closed. If a closed electrical contact is opened, the circuit 348 determines that the identification appliance has been tampered with or removed. Optionally, the identification appliance may have an indicator to indicate the status of the identification appliance.

Figure 36:
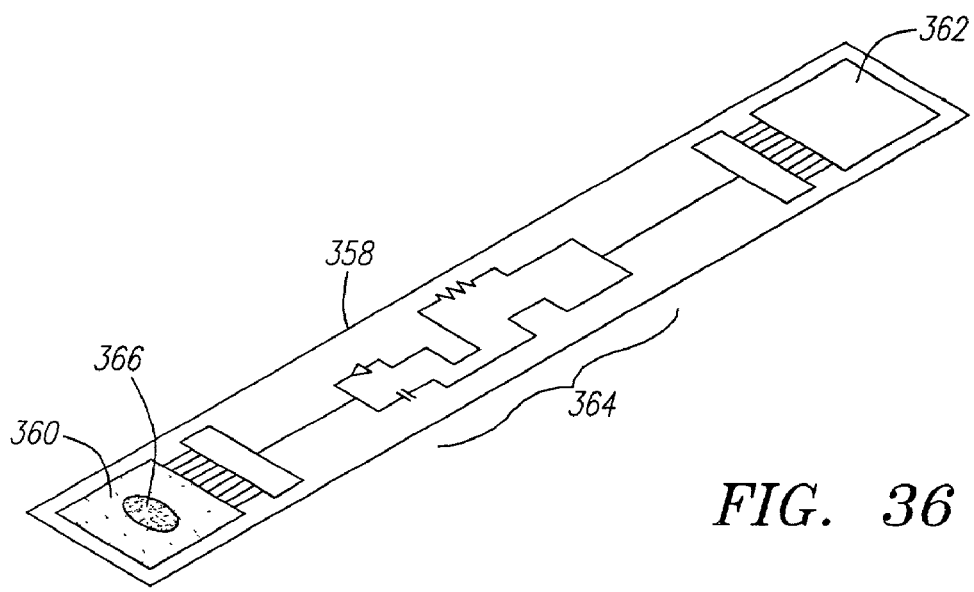
FIG. 36 is a representative illustration of an example embodiment of an improved secure identification appliance, such as an identification band, with electronic tamper detection using conductive or non-conductive glue.

FIG. 36 is a representative illustration of an example embodiment of an improved secure identification appliance, such as an identification band, with electronic tamper detection using conductive or non-conductive glue. The example identification appliance comprises an elongate body 358, a first patch of a plurality of conductive contacts 360, and a second patch of a plurality of contacts 362 that mates with the first patch of contacts 360 to form a closed electrical circuit when the band 358 is closed. Circuitry 364, which may be embedded, printed, deposited, or otherwise placed in or on the band 358 monitors whether the electrical circuits are open or closed. An adhesive gel 366 may be used to close or fasten the ends of the band 358 together. The adhesive 366 may be conductive or nonconductive. As with the embodiment of FIG. 35, the groups of contacts may be closed in a random or unpredictable pattern.

Figure 37:
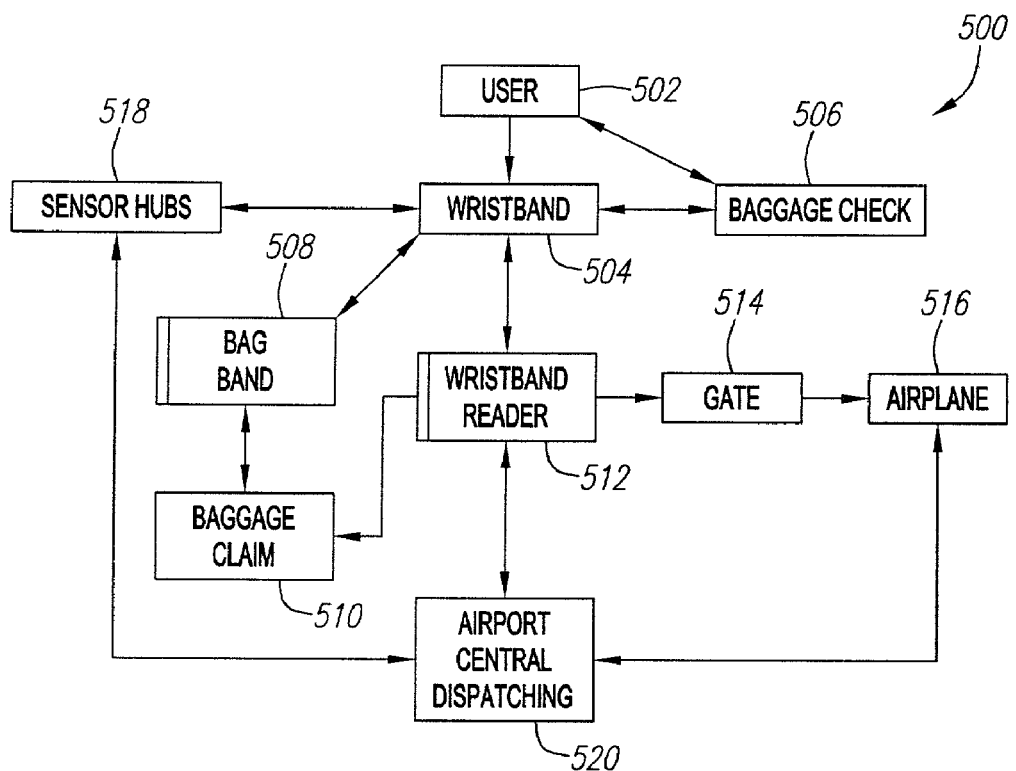
FIG. 37 is a representative illustration of an example embodiment of an airport security system that uses an improved secure identification appliance, such as an identification band.

FIG. 37 is a representative illustration of an example embodiment of an airport security system 500 that uses an improved secure identification appliance, such as an identification band. A user or passenger 502 obtains an identification appliance 504, such as a wristband, from an authorized person or agency, such as the ticket counter. When the passenger 502 checks in baggage at the ticket counter or curbside check-in 506, an identification band ("bag band") 508 is put on the baggage. The bag band 508 identifies the baggage and its owner so that when the passenger 502 goes to the baggage claim 510 to claim the baggage, corresponding data in the bag band 508 and passenger's identification appliance 504 must match. One way to determine whether there is a match is to use a band reader 512. The band reader 512 reads both the bag band 508 and passenger's identification appliance 504 and determines whether there is a match and optionally, whether there is any evidence of tampering of either. When the passenger 502 goes to the airline gate terminal 514, there may be another optional band reader to verify the identity of the passenger 502. Likewise, when the passenger 502 is about to board the aircraft 516, another optional band reader may verify the identity of the passenger 502 again. Throughout the airport, terminal, gates, restaurants, baggage areas and restrooms, there may be sensors 518 that detect and read any identification appliances 504 in their vicinity. A central airport system 520 may be coupled to the sensors 518 and band readers 512 so that the system 520 can track the whereabouts of each passenger.

Figure 38:
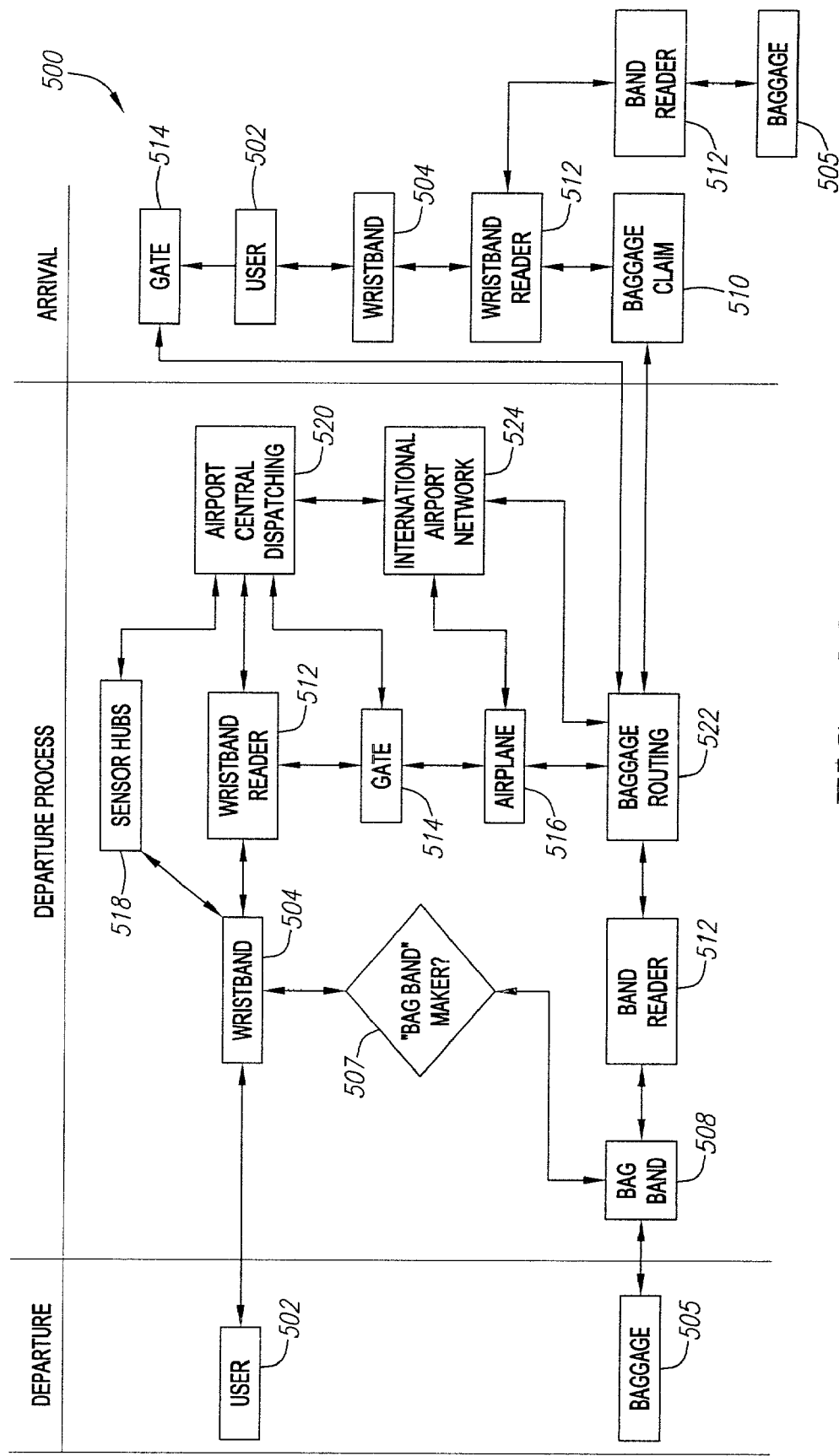
FIG. 38 is a representative illustration of another example embodiment of an airport security system that uses an improved secure identification appliance, such as an identification band.

FIG. 38 is a representative illustration of another example embodiment of an airport security system 500 that uses an improved secure identification appliance, such as an identification band. FIG. 38 illustrates an example checkin, departure and arrival process based on the airport security system 500. The left side of FIG. 38 depicts a passenger 502 and his baggage 505 prior to check-in and departure. The middle section shows the check-in and departure process. The right side of FIG. 38 illustrates the arrival process. Again, the passenger 502 obtains an identification appliance 504, such as a wristband, from an authorized person or agency, at the ticket counter or curbside checkin. When the passenger 502 checks in baggage 505 at the ticket counter or curbside check-in, a bag band machine 507 creates a bag band 508 for the baggage 505 and an identification band 504 for the passenger 502. Alternatively, the bag band machine 507 may be a bag band reader. As before, the bag band 508 identifies the baggage and its owner. A baggage routing system 522 uses the bag bands to identify baggage and other information necessary to route the baggage to its destination. Optional band readers 512 and sensors 518 may be placed at the gate 514, entry to or exit from the airplane 516, baggage claim 510 and any other area in the airport facility. The central airport system 520 may be coupled to the sensors 518 and band readers 512 so that the system 520 can track the whereabouts of each passenger as well as baggage. The central airport system 520 may be connected, if desired, to an international airport computer network 524 so that information is shared with other airports. The shared information may include an airport's information about passengers at the airport as well as international databases about known terrorists, fingerprints, etc. Thus, if airports detect that a group of known terrorists have entered into various airports at similar times, this fact can be made available to the proper authorities such as the FBI. As another example, if an airport detects the presence of several known terrorists in the airport, the airport can enter a security mode, delay flights alert the appropriate authorities, and track the terrorists. Upon arrival, the passenger 502 leaves the airplane and enters the gate 514. Again, a band reader 512 or sensor 518 may detect and ascertain the identity of the passenger 502 as he walks to the baggage claim 510. When the passenger 502 goes to the baggage claim 510 to claim his baggage 505, the bag band 508 and passenger's identification appliance 504 must match. A band reader 512 may be used to read the bag band 508 and the identification band 504. Alternatively, if bag band machine 507 is adapted to read bag bands, the bag band reader reads the bag band 508 and another band reader reads the identification band 504. The identification band 504 and bag band 508 may be deactivated upon completion of the travel event.

Any of the identification appliance embodiments may be used also by immigration officials. There are situations in which the security of a remotely readable identification appliance and data carrier require that the identification appliance can only be secured to the person by an authorized person or agency, and once secured to the person being identified, cannot be removed or its data used except by an authorized party or agency. Accordingly, the improved identification appliance can be supplied by U.S. Embassies or corresponding agencies throughout the world, which identification appliance can be encoded or encrypted with the identification and/or biometric features of the lawful bearer. The immigration authorities can read the identification appliances at the port of entry or authorized check points and compare the information retrieved from the identification appliances to information stored in their database and to biometric information obtained at the present location.

The identification appliance can be in the form of a single or multiple, detachable RFID/biometric labels that could then be detached and used to be affixed to paperwork, including a place in the Passport near the Visa seal, and that could be read and removed upon departure in order to update and close open files on visitors to the U.S., such as temporary workers, students, business visas and tourists. With regard to the immigration Green Cards issued to lawfully admitted residents, the identification appliance can be in the form of a temporary RFID/biometrics technology based label or card that identifies the bearer between the time of entry or admission to the U.S., and the mailing of the permanent card to the legal alien.

An additional use for the identification appliance would be to identify applicants for driver's licenses throughout the country. Driver's licenses are restricted to applicants who have proper and lawful identification that proves either proper citizenship or legal resident status. Exceptions are people with business visas on a temporary stay, some temporary working visas and perhaps people under student visas. An identification appliance with biometrics can be used to prove a person's identity and right to apply for a driver's license.

In any of the embodiments, the identification appliance may include optional structures and features, such as any of the features described below. For example, the communication circuit may perform a communication function of any type and frequency, can communicate passively such as a transponder and/or actively by initiating communications, and can use low or high frequencies. The identification appliance may operate in the low frequency, high frequency, UHF, SHF, or microwave radio bands.

The identification appliance may be attached to an article in which a circuit in the identification appliance performs an optional electronic article surveillance (EAS) function, for example, to prevent the theft of the article. The EAS function does not transmit an identification code, but enables a reader to detect if the identification appliance is near the reader, for example, at the entry or exit to a retail store or building.

The identification appliance may provide its location to another device, for example, over a small area (e.g., a room or a building) or a large area (e.g., countrywide or worldwide). Such location information may be provided with a varying degree of accuracy such as with a less than 1 meter uncertainty to a greater than 1 kilometer uncertainty. The location function may be accomplished by calculations derived by the identification appliance of signals received by it (such as from a Global Positioning System or a Local Positioning System), or the location may be derived externally to the identification band, such as by a matrix of RF receivers responding to the strength or timing of reception of signals received from the identification band.

Optionally, the identification appliance may receive a command from a wireless communication system or network. The wireless communication system may transmit the command to a single identification appliances, to all identification appliances within range, or to a subset of identification appliances. The command may be any kind of command. The command can change any operating characteristic or function of the identification appliance, or cause the identification appliance to execute any set of instructions. For instance, the command can change any human perceptible indicator in the improved identification appliance such as the display, light, audible signal generator, vibrator and the like. As another example, the command may change the frequency at which information is received and/or transmitted between the identification appliance and an external communication system or network. By changing the frequency of transmission or reception, the identification appliance can reduce interference with other identification appliances in the area when the identification appliance is communicating wirelessly with an external device. As yet another example, the command may change the ability of the identification appliance to receive and/or transmit data, the validity of data in the identification appliance, a password to communicate with the identification appliance, the level or type of encryption of data, the expiration of the identification appliance (e.g., the identification appliance is deemed invalid after it expires), a characteristic in the communications protocol (e.g., baud rate or speed of communications, error correction format, communication header format) so that the identification appliance can be able to communicate with different types of communication networks, and virtually any other operating characteristic or function. The command may also optionally give privileges to the improved identification appliance that the wearer of the identification appliance did not have previously. For example, a wireless communication network may permit the wearer of an improved identification appliance to enter a restricted area, where the permission is time-sensitive and time-limited (e.g., the permission begins at a certain time and expires at a certain time).

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions shown in the process flow diagrams described herein is merely illustrative, and the invention can be performed using different or additional process actions, or a different combination or ordering of process actions. As another example, each feature of one embodiment can be mixed and matched with other features shown in other embodiments. Features and processes known to those of ordinary skill in the art of identification appliances may similarly be incorporated as desired. Additionally and obviously, features may be added or subtracted as desired. Accordingly, the invention is not to be restricted except in light of the attached claims and their equivalents.

What is claimed is:

1. An identification appliance adapted to provide information about a person, the identification appliance comprising: a programmable data storage device to receive and store identification information for positively identifying a person; a structure adapted to be worn by or attached to the person, said structure carrying said data storage device; a fastener disposed in or on the structure, the fastener being adapted to attach the structure to the person; a circuit disposed in or on the structure and electrically coupled to the fastener, a closing of the fastener enables a function of the circuit, and said circuit being adapted to alter, erase, or damage the identification information if the circuit determines that the identification appliance has been tampered with; and a biometric sensor coupled to the circuit and disposed in or on the structure, the biometric sensor being adapted to receive biometric information about the person from a source external to the identification appliance and to communicate the biometric information to the data storage device; wherein the biometric sensor includes a light-emitting device adapted to emit light towards the person and a light-sensing device adapted to measure light reflection off the person to obtain a fingerprint charcteristic.

2. The identification appliance of claim 1 wherein the circuit function includes a communication of the information about the person external to the identification appliance.

3. The identification appliance of claim 1 wherein the circuit function includes a supply of power to the circuit.

4. The identification appliance of claim 1 wherein the circuit function includes an enablement of an antenna.

5. The identification appliance of claim 1 wherein the circuit function includes a tuning of an antenna.

6. The identification appliance of claim 1 wherein the circuit function includes changing a logic state input to the circuit.

7. The identification appliance of claim 1 wherein the structure is elongate and flexible.

8. The identification appliance of claim 1 wherein the circuit includes a radio frequency identification circuit, the radio frequency identification circuit adapted to transmit the information by radio frequency communication to an external device.

9. The identification appliance of claim 1 wherein the fastener comprises a first contact and a second contact and the circuit determines whether the first and second contacts are in communication with each other.

10. The identification appliance of claim 1 further comprising an electrical conductor which, when the fastener is closed, couples the fastener to the circuit.

11. The identification appliance of claim 1 wherein the information includes biometric data.

12. The identification appliance of claim 1 wherein the information includes an image of a feature of the person.

13. The identification appliance of claim 1 wherein the information include optical character recognizable data.

14. The identification appliance of claim 1 wherein the identification appliance is a wristband, headband, armband, ankleband, neckband, or legband.

15. The identification appliance of claim 1 wherein the identification appliance is a patch or card.

16. The identification appliance of claim 1 wherein at least a circuit component of the circuit is formed substantially of at least one organic material.

17. The identification appliance of claim 1 further comprising a power source coupled to supply power to the circuit, the power source being formed at least partially of an organic material.

18. The identification appliance of claim 1 further comprising a diode within the circuit, the diode comprising an organic material.

19. The identification appliance of claim 1 wherein said data storage device is formed substantially of at least one organic material.

20. The identification appliance of claim 1 further comprising a microstrip antenna coupled to the circuit, the antenna being adapted to transmit the information to a device external to the identification appliance.

21. The identification appliance of claim 1 further comprising an audio or visual display coupled to the circuit.

22. The identification appliance of claim 1 wherein the information includes medical data about the person.

23. The identification appliance of claim 1 further comprising an indicator, the indicator adapted to indicate whether the identification appliance has been tampered with.

24. The identification appliance of claim 1 further comprising an indicator, the indicator adapted to indicate whether the fastener is closed.

25. The identification appliance of claim 1 wherein the biometric information includes a retina, fingerprint, iris, voice, or genetic characteristic of the person.

26. The identification appliance of claim 1 wherein the biometric information includes an image of the person.

27. The identification appliance of claim 1 wherein the biometric information include optical character recognizable data.

28. The identification appliance of claim 1 wherein the biometric sensor includes a light-emitting device adapted to emit light towards the person and a light-sensing device adapted to measure light reflection off the person to obtain a retinal characteristic.

29. The identification appliance of claim 1 wherein the biometric sensor is formed of at least one organic material.

30. The identification appliance of claim 1 wherein the sensor includes an acoustic sensor adapted to receive acoustic information about the person.

31. The identification appliance of claim 30 wherein the acoustic sensor is formed substantially of at least one organic material.

32. The identification appliance of claim 1 wherein the sensor includes an optical sensor adapted to receive information bout the person optically.

33. The identification appliance of claim 32 wherein the optical sensor is formed of at least one organic material.

34. The identification appliance of claim 1 wherein the sensor includes a chemical sensor adapted to receive the information about the person chemically.

35. The identification appliance of claim 34 wherein the chemical sensor is adapted to assay the biochemical content of the person's scent, blood, or breath.

36. The identification appliance of claim 1 wherein the sensor includes a humidity sensor adapted to receive information about the humidity.

37. The identification appliance of claim 1 wherein the sensor includes a heat sensor adapted to receive temperature information.

38. The identification appliance of claim 1 wherein the sensor includes a pressure sensor adapted to receive pressure information.

39. The identification appliance of claim 1 wherein the sensor includes an electromagnetic sensor adapted to receive electromagnetic energy.

40. The identification appliance of claim 1 wherein the sensor is formed of at least one organic material.

41. The identification appliance of claim 1 further comprising a keypad coupled to the data storage device, the keypad adapted to input information into the data storage device.

42. The identification appliance of claim 1 further comprising an indicator, the indicator adapted to indicate whether the identification appliance has been tampered with.

43. The identification appliance of claim 42 wherein said indicator is adapted to release a substance perceptible to an animal.

44. The identification appliance of claim 42 wherein said indicator is adapted to release a substance perceptible to a machine.

45. An identification appliance adapted to provide information about a person, the identification appliance comprising: a programmable data storage device to receive and store identification information for positively identifying a person; a structure adapted to be worn by or attached to the person, said structure carrying said data storage device; a fastener disposed in or on the structure the fastener being adapted to attach the structure to the person; a circuit disposed in or on the structure and electrically coupled to the fastener, a closing of the fastener enables a function of the circuit, and said circuit being adapted to alter, erase, or damage the idenification information if the circuit determines that the identification appliance has been tampered with; and a biometric sensor coupled to the ciruit and disposed in or on the structure, the biometric sensor being adapted to receive biometric information about the person from a source external to the identification appliance and to communicate the biometric informatin to the data storage device; wherein the sensor includes an acoustic sensor adapted to receive acoustic information about the person; and wherein the acoustic sensor is adapted to receive speech information from the person and the circuit is adapted to process the speech information.

46. The identification appliance of claim 45 wherein the circuit is adapted to derive a unique identifying information about the person from the speech information.

47. The identification appliance of claim 45 wherein the circuit includes an audio generation circuit adapted to output synthesized speech.

48. An identification appliance adapted to provide information about a person, the identification appliance comprising: a programmable data storage device to receive and store identification information for positively identifying a person; a structure adapted to be worn by or attached to the person, said structure carrying said data storage device; a fastener disposed in or on the structure, the fastener being adapted to attach the structure to the person; and a circuit disposed in or on the structure and electrically coupled to the fastener, a closing of the fastener enables a function of the circuit, and said circuit being adapted to alter, erase, or damage the identification information if the circuit determines that the identificaitoin appliance has been tampered with; and a biometric sensor coupled to the circuit and disposed in or on the structure, the biometric sensor being adated to receive boiometric information about the person from a source external to the identification appliance and to communicate the biometric information to the data storage device; wherein the sensor includes an acoustic sensor adapted to receive acoustic information about the persons; and wherein the acoustic sensor comprises a piezoelectric transducer.

49. An identification appliance adapted to provide informatin about a person, the identification appliance comprising; a programmable data storage device to receive and store identification information for positvely identifying a person; a structure adapted to be worn by or attached to the person, said structure carrying said data storage device; a fastener disposed in or on the structure, the fastener being adapted to attach the structure to the person; and a circuit disposed in or on the structure and electrically coupled to the fastener, a closing of the fastener enables a function of the circuit, and said circuit being adapted to alter, erase, or damage the identification information if the circuit determines that the identification appliance has been tampered with; and a biometric sensor coupled to the circuit and disposed in or on the structure, the biometric sensor being adapted to receive biometric informatin about the person from a source external to the identification appliance and to communicate the biometric informatin to the data storage device; wherein the sensor includes an optical sensor adapted to receive information about the person optically; and wherein the optical sensor comprises a light detector adapted to capture images of the person's face, fingerprint, iris, or retina.

50. The identification appliance of claim 49 wherein the optical sensor includes a charge coupled device.

51. The identification appliance of claim 49 wherein the optical sensor includes a photodetector.

52. An identification appliance adapted to provide information about a person, the identification appliance comprising: a programmable data storage device to receive and store identification information for positively identifying a person; a structure adapted to be worn by or attached to the person, said structure carrying said data storage device; a fastener disposed in or on the structure, the fastener being adapted to attach the structure to the person: a circuit disposed in or on the structure and electrically coupled to the fastener, a closing of the fastener enables a function of the circuit, and said circuit being adapted to alter, erase, or damage the identification information if the circuit determines that the identification appliance has been tampered with; a biometric sensor coupled to the circuit and disposed in or on the sturcture, the biometric sensor being adapted to receive biometric informatin about the person from a source external to the identification appliance and to communiciate the biometric information to the data storage device; and an idicator adpated to indicate whether the identification appliance has been tampered with; wherein the indicator comprises an ink or dye, the indicator adapted to release the ink or dye when the circuit detects tampering with the identification appliance.

53. An identification appliance adapted to provide information about a person, the identification appliance comprising: a programmable data storage device to receive and store identification information for positively identifying a person; a structure adapted to be worn by or attached to the person, said structure carrying said data storage device; a fastener disposed in or on the structure, the fastener being adapted to attach the structure to the person; a circuit disposed in or on the structure and electrically coupled to the fastener, a closing of the fastener enables a function of the circuit, and said circuit being adapted to alter, erase, or damage the identification information if the circuit determines that the identification appliance has been tampered with; and-an indicator adapted to indicate whether the identification appliance has been tampered with, the indicator comprising an ink or dye, the indicator adapted to release the ink or dye when the circuit detects tampering with the identification appliance; and a biometric sensor coupled to the circuit and disposed in or on the structrure, the biometric sensor being adapted to receive biometric information about the person from a source external to the identification appliance and to communicate the biometric information to the data storage device; wherein the biometric sensor includes a light-emitting device adapted to emit light towards the person and a light-sensing device adapted to measure light reflection off the person to obtain a retinal characteristic.

54. The identification appliance of claim 53 wherein said indicator is adapted to release a substance perceptible to an animal.

55. The identification appliance of claim 53 wherein said indicator is adapted to release a substance perceptible to a machine.

56. The identification appliance of claim 53 wherein the circuit function includes a communication of the information about the person external to the identification appliance.

57. The identification appliance of claim 53 wherein the circuit function includes a supply of power to the circuit.

58. The identification appliance of claim 53 wherein the circuit function includes an enablement of an antenna.

59. The identification appliance of claim 53 wherein the circuit function includes a tuning of an antenna.

60. The identification appliance of claim 53 wherein the circuit function includes changing a logic state input to the circuit.

61. The identification appliance of claim 53 wherein the structure is elongate and flexible.

62. The identification appliance of claim 53 wherein the circuit includes a radio frequency identification circuit, the radio frequency identification circuit adapted to transmit the information by radio frequency communication to an external device.

63. The identification appliance of claim 53 wherein the fastener comprises a first contact and a second contact and the circuit determines whether the first and second contacts are in communication with each other.

64. The identification appliance of claim 53 further comprising an electrical conductor which, when the fastener is closed, couples the fastener to the circuit.

65. The identification appliance of claim 53 wherein the information includes biometric data.

66. The identification appliance of claim 53 wherein the information includes an image of a feature of the person.

67. The identification appliance of claim 53 wherein the information include optical character recognizable data.

68. The identification appliance of claim 53 wherein the identification appliance is a wristband, headband, armband, ankleband, neckband, or legband.

69. The identification appliance of claim 53 wherein the identification appliance is a patch or card.

70. The identification appliance of claim 53 wherein at least a circuit component of the circuit is formed substantially of at least one organic material.

71. The identification appliance of claim 53 further comprising a power source coupled to supply power to the circuit, the power source being formed at least partially of an organic material.

72. The identification appliance of claim 53 further comprising a diode within the circuit, the diode comprising an organic material.

73. The identification appliance of claim 53 wherein said data storage device is formed substantially of at least one organic material.

74. The identification appliance of claim 53 further comprising a microstrip antenna coupled to the circuit, the antenna being adapted to transmit the information to a device external to the identification appliance.

75. The identification appliance of claim 53 further comprising an audio or visual display coupled to the circuit.

76. The identification appliance of claim 53 wherein the information includes medical data about the person.

77. The identification appliance of claim 53 further comprising an indicator, the indicator adapted to indicate whether the identification appliance has been tampered with.

78. The identification appliance of claim 53 further comprising an indicator, the indicator adapted to indicate whether the fastener is closed.

79. The identification appliance of claim 53 wherein the biometric information includes a retina, fingerprint, iris, voice, or genetic characteristic of the person.

80. The identification appliance of claim 53 wherein the biometric information includes an image of the person.

81. The identification appliance of claim 53 wherein the biometric information include optical character recognizable data.

82. The identification appliance of claim 53 wherein the biometric sensor includes a light-emitting device adapted to emit light towards the person and a light-sensing device adapted to measure light reflection off the person to obtain a fingerprint characteristic.

83. The identification appliance of claim 53 wherein the biometric sensor is formed of at least one organic material.

84. The identification appliance of claim 53 wherein the sensor includes an acoustic sensor adapted to receive acoustic information about the person.

85. The identification appliance of claim 84 wherein the acoustic sensor comprises a piezoelectric transducer.

86. The identification appliance of claim 84 wherein the acoustic sensor is formed substantially of at least one organic material.

87. The identification appliance of claim 53 wherein the sensor includes an optical sensor adapted to receive information about the person optically.

88. The identification appliance of claim 87 wherein the optical sensor is formed of at least one organic material.

89. The identification appliance of claim 53 wherein the sensor includes a chemical sensor adapted to receive the information about the person chemically.

90. The identification appliance of claim 89 wherein the chemical sensor is adapted to assay the biochemical content of the person's scent, blood, or breath.

91. The identification appliance of claim 53 wherein the sensor includes a humidity sensor adapted to receive information about the humidity.

92. The identification appliance of claim 53 wherein the sensor includes a heat sensor adapted to receive temperature information.

93. The identification appliance of claim 53 wherein the sensor includes a pressure sensor adapted to receive pressure information.

94. The identification appliance of claim 53 wherein the sensor includes an electromagnetic sensor adapted to receive electromagnetic energy.

95. The identification appliance of claim 53 wherein the sensor is formed of at least one organic material.

96. The identification appliance of claim 53 further comprising a keypad coupled to the data storage device, the keypad adapted to input information into the data storage device.

97. An identification appliance adapted to provide information about a person, the identification appliance comprising: a programmable data storage device to receive and store identification information for positively identifying a person; a structure adapted to worn by or attached to the person, said structure carrying said data storage device; a fastener dispossed in or on the structure, the fastener being adapted to attach the structure to the person; a circuit disposed in or on the structure and electrically coupled to the fastener, aclosing of the fastener enables a function of the circuit, and said circuit being adapted to after, erase, or damage the identification information if the circuit determines that the idntification appliance has been tampered with; and indicator adapted to indicate whether the identification appliance has been tampered with, the indicator comprising an ink or dye, the indicator adapted to release the ink or dye when the circuit detects tampering with the identification appliance; a biometric sensor coupled to the circuit and disposed in or on the structure, the boimetric sensor being adapted to receive biometric informatio about the person from a source external to the identification appliance and to communicate the biometric information to the data storage device; wherein the sensor includes an acoustic sensor adapted to receive acoustic information about the person; and wherein the acoustic sensor is adapted to receive speech information from the person and the circuit is adapted to process the speech information.

98. The identification appliance of claim 97 wherein the circuit is adapted to derive a unique identifying information about the person from the speech information.

99. The identification appliance of claim 97 wherein the circuit includes an audio generation circuit adapted to output synthesized speech.

100. An identification appliance adapted to provide information about a person, the identification appliance comprising: a programmable data storage devcie to receive and store identification information for positively identifying a person; a structure adapted to be worn by or attached to the person, said structure carrying said data storage device; a fastener disposed in or on the structure, the fastener being adapted to attach the structure to the person; a circuit dsiposed in or on the structure and electrically coupled to the fastener, a closing of the fastener enables a function of the circuit and said circuit being adapted to alter, erase, or damage the identification information if the circuit determnes that the identification apliance has been tampered with; an indicator adapted to indicate whether the identification appliance has been tampered with, the indicator comprising an ink or dye, the indicator adapted to release the ink or dye when the circuit detects tampering with the identification apliance; a biometric sensor coupled to the circuit and disposed in or on the structure, the biometric sensor being adapted to receive biometric information about the person from a source external to the identification appliance and to communicate the biometric information to the data storage device; wherein the sensor includes an optical sensor adapted to receive information about the person optically; and wherein the optical sensor comprises a light detector adapted to capture images of the person's face, fingerprint, iris, or retina.

101. The identification appliance of claim 100 wherein the optical sensor includes a charge coupled device.

102. The identification appliance of claim 100 wherein the optical sensor includes a photodetector.

103. An identification appliance adapted to provide information about a person, the identification appliance comprising: a programmable data storage device to receive and store identification information for positively identifying a person; a structure adapted to be worn by or attached to the person, said structure carrying said data storage device; a fastener disposed in or on the structure, the fastener being adapted to attach the structure to the person; a circuit disposed in or on the structure and electrically coupled to the fastener, a closing of the fastener enables a function of the circuit, and said circuit being adapted to alter, erase, or damage the identification information if the circuit determines that the identification appliance has been tampered with; and a biometric sensor coupled to the circuit and disposed in or on the structure, the biometric sensor being adapted to receive biometric information about the person from a source external to the identification appliance and to communicate the biometric information to the data storage device; wherein the biometric sensor includes a light-emitting device adapted to emit light towards the person and a light-sensing device adapted to measure light reflection off the person to obtain a retinal characteristic.

104. An identification appliance adapted to provide information about a person, the identification appliance comprising: a programmable data storage device to receive and store identification information for positively identifying a person; a structure adapted to be worn by or attached to the person, said structure carrying said data storage device; a fastener disposed in or on the structure, the fastener being adapted to attach the structure to the person; a circuit disposed in or on the structure and electrically coupled to the fastener, a closing of the fastener enables a function of the circuit, and said circuit being adapted to alter, erase, or damage the identification information if the circuit determines that the identification appliance has been tampered with; an indicator adapted to indicate whether the identification appliance has been tampered with, the indicator comprising an ink or dye, the indicator adapted to release the ink or dye when the circuit detects tampering with the identification appliance; and a biometric sensor coupled to the circuit and disposed in or on the structure, the biometric sensor being adapted to receive biometric information about the person from a source external to the identification appliance and to communicate the biometric information to the data storage device; wherein the biometric sensor includes a light-emitting device adapted to emit light towards the person and a light-sensing device adapted to measure light reflection off the person to obtain a fingerprint characteristic.

105. An identification appliance adapted to provide information about a person, the identification appliance comprising: a programmable data storage device to receive and store identification information for positively identifying a person; a structure adapted to be worn by or attached to the person, said structure carrying said data storage device; a fastener disposed in or on the structure, the fastener being adapted to attach the structure to the person; a circuit disposed in or on the structure and electrically coupled to the fastener, a closing of the fastener enables a function of the circuit, and said circuit being adapted to alter, erase, or damage the identification information if the circuit determines that the identification appliance has been tampered with; an indicator adapted to indicate whether the identification appliance has been tampered with, the indicator comprising an ink or dye, the indicator adapted to release the ink or dye when the circuit detects tampering with the identification appliance; and a biometric sensor coupled to the circuit and disposed in or on the structure, the biometric sensor being adapted to receive biometric information about the person from a source external to the identification appliance and to communicate the biometric information to the data storage device; wherein the acoustic sensor is adapted to receive speech information from the person and the circuit is adapted to process the speech information; and wherein the acoustic sensor comprises a piezoelectric transducer.

* * * * *